(12) United States Patent
Tomasini-Johansson et al.

(10) Patent No.: US 10,828,372 B2
(45) Date of Patent: Nov. 10, 2020

(54) COMPOSITIONS AND METHODS FOR THE INHIBITION OF FIBROSIS

(71) Applicant: WISCONSIN ALUMNI RESEARCH FOUNDATION, Madison, WI (US)

(72) Inventors: Bianca R. Tomasini-Johansson, Madison, WI (US); Glen S. Kwon, Madison, WI (US); Pawel Waldemar Zbyszynski, Chicago, IL (US); Nathan Sandbo, Middleton, WI (US); Ksenija Bernau, Madison, WI (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 0 days.

(21) Appl. No.: 16/186,864

(22) Filed: Nov. 12, 2018

(65) Prior Publication Data

US 2019/0142956 A1 May 16, 2019

Related U.S. Application Data

(60) Provisional application No. 62/584,360, filed on Nov. 10, 2017.

(51) Int. Cl.
| | | |
|---|---|---|
| *A61K 47/60* | (2017.01) | |
| *A61P 43/00* | (2006.01) | |
| *A61P 13/12* | (2006.01) | |
| *A61K 9/00* | (2006.01) | |
| *A61K 38/16* | (2006.01) | |
| *A61K 45/06* | (2006.01) | |
| *A61K 49/00* | (2006.01) | |

(52) U.S. Cl.
CPC ............ *A61K 47/60* (2017.08); *A61K 9/0019* (2013.01); *A61K 9/0029* (2013.01); *A61K 38/164* (2013.01); *A61K 45/06* (2013.01); *A61K 49/0056* (2013.01); *A61P 13/12* (2018.01); *A61P 43/00* (2018.01)

(58) Field of Classification Search
None
See application file for complete search history.

(56) References Cited

U.S. PATENT DOCUMENTS

| 9,364,516 B2 | 6/2016 | Sottile et al. | |
|---|---|---|---|
| 2018/0231558 A1* | 8/2018 | Lyden | G01N 33/57438 |

FOREIGN PATENT DOCUMENTS

| EP | 3257862 | * 12/2017 |
|---|---|---|
| WO | 2011097401 A1 | 8/2011 |
| WO | 2013062544 A1 | 5/2013 |

OTHER PUBLICATIONS

International Search Report dated Jan. 17, 2019; International Application No. PCT/US2018/060291; International Filing Date: Nov. 12, 2018 (7 pages).

Lee et al., "Synthesis, Characterization, and Pharmacokinetic Studies of PEGylated Glucagon-like Peptide-1"; Bioconjugate Chem. 2005, 16, pp. 377-382.

Written Opinion dated Jan. 17, 2019; International Application No. PCT/US2018/060291; International Filing Date: Nov. 12, 2018 (9 pages).

Bailon et al.; Rational Design of a Potent, Long-Lasting Form of Interferon: A 40 kDa Branched Polyethylene Glycol-Conjugated Interferon a-2a for the Treatment of Hepatitis C; Bioconjugate Chem; 12; pp. 195-202; (2001).

Dolman et al.; "Drug Targeting to the Kidney: Advances in the Active Targeting of Therapeutics to Proximal Tubular Cells"; Advanced Drug Delivery Reviews; 62; pp. 1344-1357; (2010).

Elder et al.; "Effects on Peptide Binding Affinity for TNFa by PEGylation and Conjugation to Hyaluronic Acid"; European Polymer Journal; 49; pp. 2968-2975; (2013).

Ensenberger et al.; "Specific Interactions Between F1 Adhesin of *Streptococcus pyogenes* and N-terminal Modules of Fibronectin"; Journal of Biological Chemistry: 276(38) pp. 35606-35613; (2001).

Knauf et al., "Relationship of Effective Molecular Size to Systemic Clearance in Rats of Recombinant Interleukin-2 Chemically Modified with Water-soluble Polymers"; Journal of Biological Chemistry; 263(29); pp. 15064-15070; (1988).

Maurer et al.; "Extended Binding Site on Fibronectin for the Functional Upstream Domain of Protein F1 of *Streptococcus pyogenes*"; Journal of Biological Chemistry; 285(52); pp. 51087-41099; (2010).

Pasut et al.; "State of the art in PEGylation: The Great Versatility Achieved After Forty Years of Research"; Journal of Controlled Release; 161; pp. 461-472; (2012).

Ross et al.; "Binding and Functional Studies with the Growth Hormone Receptor Antagonist, B2036-PEG (Pegvisomant), Reveal Effects of Pegylation and Evidence That It Binds to a Receptor Dimer"; The Journal of Clinical Endocrinology & Metabolism; 86(4); pp. 1716-1723; (2001).

Selis et al.; "Pegylated Trastuzumab Fragments Acquired on Increase in Vivo Stability but Show a Largely Reduced Affinity for the Target Antigen"; Int J. Mol. Sci.; 17; p. 491, 15 pages; (2016).

Tomasini-Johansson et al.; "PEGylated pUR4/FUD Peptide Inhibitor of Fibronectin Fibrillogenesis Decreases Fibrosis in Murine Unilateral Ureteral Obstruction Model of Kidney Disease"; PLoS One; 13(10); e025350, 23 pages, (2018).

Zbyszynski et al. "Characterization of the PEGylated Functional Upstream Domain Peptide (PEG-FUD): a Potent Fibronectin Assembly Inhibitor with Potential as an Anti-Fibrotic Therapeutic"; Pharm Res; 35; 126; 10 pages; (2018).

* cited by examiner

*Primary Examiner* — Maury A Audet
(74) *Attorney, Agent, or Firm* — Cantor Colburn LLP

(57) ABSTRACT

Described herein is a mono-end PEGyated functional upstream domain (FUD), pharmaceutical compositions, and its use to inhibit fibrosis such as organ fibrosis, idiopathic pulmonary fibrosis and fibrosis associated with cancer. Also included are methods of probing for injured or repairing tissue in an individual in need thereof using the mono-end PEGyated-FUD.

20 Claims, 28 Drawing Sheets
(13 of 28 Drawing Sheet(s) Filed in Color)
Specification includes a Sequence Listing.

IHC Fibronectin

US 10,828,372 B2

COMPOSITIONS AND METHODS FOR THE INHIBITION OF FIBROSIS

CROSS-REFERENCE TO RELATED APPLICATIONS

This application claims priority to U.S. Provisional Application Ser. No. 62/584,360 filed on Nov. 10, 2017, which is incorporated herein by reference in its entirety.

STATEMENT REGARDING FEDERALLY SPONSORED RESEARCH & DEVELOPMENT

This invention was made with government support under CA179738, AI101157 and CA206458 awarded by the National Institutes of Health. The government has certain rights in the invention.

FIELD OF THE DISCLOSURE

The present disclosure is related to modified fibronectin-binding peptides and their use to inhibit fibrosis.

BACKGROUND

Organ fibrosis presents an important clinical challenge that requires improved treatments. Fibrosis in general refers to excessive extracellular matrix (ECM) deposition resulting from chronic injury that minimizes apoptotic and necrotic damage done by sustained inflammation. This process can affect major organs such as the liver, kidneys, and lungs. Current therapies for fibrosis include modulators of cellular pathways such as corticosteroids, TGF-β agonists and receptor inhibitors, and ACE inhibitors. These approaches, however, are often ineffective in reverting fibrotic morphology and can be accompanied by adverse pleiotropic effects.

Targeting ECM components remains a largely unexplored path that has a therapeutic potential alongside already established tools. Because deposition of collagen is a cornerstone of the progression of fibrotic pathology, its modulation is a promising target for a therapeutic strategy. Research has pointed to fibronectin (FN) as one such target because of its role in laying a scaffold for collagen fibrillogenesis as well as in the infiltration of leukocytes and thus progression of organ inflammation. This hypothesis was previously tested in the liver fibrosis model using the functional upstream domain (FUD) peptide. FUD is an inhibitor of FN that binds with nanomolar affinity specifically to the 70K N-terminal domain of FN involved in fibrillogenesis. FUD was effective at ameliorating symptoms in the liver fibrosis and coronary artery disease models. It was found that treatment with FUD diminishes fibronectin and collagen ECM levels in vitro, normalizes morphology of injured tissue, and improves liver function in vivo. Without being held to theory, it is believed that the effectiveness of FUD is challenged by a short half-life as is often the case for protein and peptide therapeutics.

What is needed are improved anti-fibrotic compositions and methods of inhibiting fibrosis.

BRIEF SUMMARY

In one aspect, described herein is mono-end-PEGylated FUD and its pharmaceutical compositions.

In another aspect, method of inhibiting fibrosis in a subject in need thereof, comprises administering to the subject a therapeutically effective amount of the mono-end-PEGylated FUD.

In yet another aspect, a method of inhibiting cancer metastasis, comprises administering to a subject at risk for cancer metastasis the mono-end-PEGylated FUD.

In yet another aspect, a method of probing for injured or repairing tissue in an individual in need thereof, comprising administering to the individual a diagnostic amount of the mono-end-PEGylated FUD described herein.

BRIEF DESCRIPTION OF THE DRAWINGS

The patent or application file contains at least one drawing executed in color. Copies of this patent or patent application publication with color drawings will be provided by the Office upon receipt and payment of the necessary fee.

Figure 1:
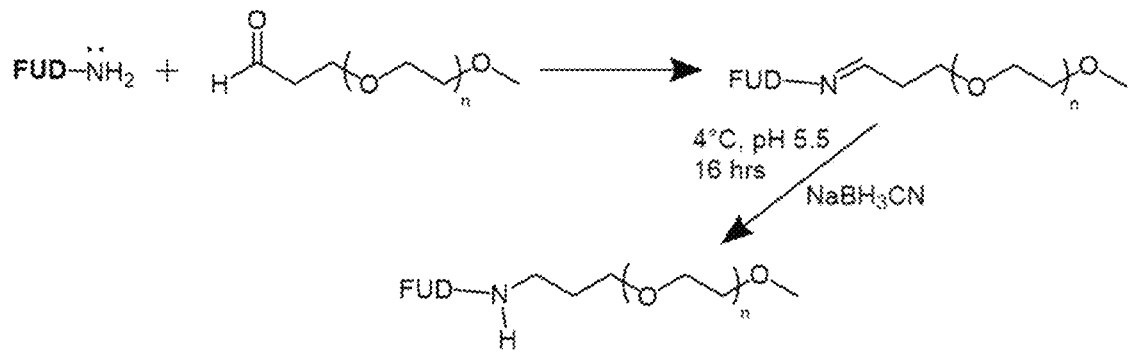
FIG. 1 shows N-terminus specific chemistry was used to synthesize 10 kDa, 20 kDa, and 40 kDa PEG-FUD conjugates.

The above-described and other features will be appreciated and understood by those skilled in the art from the following detailed description, drawings, and appended claims.

DETAILED DESCRIPTION

FUD, specifically the His-tagged form of FUD, has been reported to decrease fibronectin (FN) and collagen in murine models of carotid artery disease and liver fibrosis. When the His-tagged form of FUD was tested by the inventors for its ability to decrease fibronectin and collagen in an acute model of kidney disease, the Unilateral Ureteral Obstruction (UUO) model, non-specificity with the His-tagged peptides was encountered. Because PEGylation typically results in a loss of binding affinity, it was unexpected that FUD and PEG-FUD would have a similar binding affinity for fibronectin. Based on the prior art, PEG-FUD, due to its relatively large size and expected low renal clearance, was not expected to be effective in treating kidney fibrosis. Unexpectedly, end-PEGylated FUD (PEG-FUD) was effective when testing the conjugate in the UUO model for its ability to decrease fibronectin, collagen, leukocyte infiltration and to preserve proximal tubular structure. Also unexpectedly, PEG-FUD treatment initiated after the onset of bleomycin-induced lung injury and fibrosis significantly improves survival and reduces overall lung fibrosis.

In addition, FN is shown to be increased in certain tumors, such as breast carcinoma, where it is associated with poor prognosis. FN has been implicated in tumor growth, resistance to apoptosis, amelioration of immune response to tumors, and angiogenesis, among other pro-tumorigenic characteristics. In a variety of microenvironments, FN is also pivotal to collagen deposition and thereby, tissue density, which affects tumor progression. Because FN fibrillogenesis is tightly regulated, FN assembly is a valid target for anti-tumor therapy. For example, inhibiting FN fibril formation will decrease tumor growth and possibly metastasis. It has been unexpectedly shown that both the unconjugated FUD and PEG-FUD inhibit tumor volume in murine models of breast cancer.

The 49 amino acid FUD peptide, also called PUR4, has the sequence:

SEQ ID NO: 1
KDQSPLAGESGETEYITEVYGNQQNPVDIDKKLPNETGFSGNMVETEDT

As used herein, FUD includes both L-FUD and D-FUD. All of the examples herein were performed with L-FUD, however, D-FUD is expected to act equivalently with reduced immunogenicity. As used herein, FUD also includes variant amino acid sequences which have substantial identity with SEQ ID NO: 1, so long as the variant binds the 70K N-terminal domain of fibronectin with at least nanomolar affinity. The term "substantial identity" means that, when SEQ ID NO: 1 and a variant amino acid sequence are aligned to match each other as much as possible and the aligned sequences are analyzed using an algorithm that is ordinarily used in the art, SEQ ID NO: 1 has at least 80% sequence identity, preferably at least 90%, and more preferably at least 95% sequence identity compared to the variant amino acid sequence. In another aspect, the FUD sequence can have 1-5 amino acid substitutions, additions or deletions so long as the variant binds the 70K N-terminal domain of fibronectin with at least nanomolar affinity.

A variant means a peptide which has a different sequence from the amino acid sequence of SEQ ID NO: 1 by a deletion, an insertion, a non-conservative or conservative substitution of at least one amino acid residue, or a combination thereof.

The most commonly occurring exchanges are changes between amino acid residues Ala/Ser, Val/Ile, Asp/Glu, Thr/Ser, Ala/Gly, Ala/Thr, Ser/Asn, Ala/Val, Ser/Gly, Thy/Phe, Ala/Pro, Lys/Arg, Asp/Asn, Leu/Ile, Leu/Val, Ala/Glu, and Asp/Gly.

As used herein, the term "PEGylation" refers to the covalent conjugation of a polyethylene glycol (PEG) to a FUD peptide, the polyethylene glycol (PEG) derivative including a structural formula expressed by $CH_3O—(CH_2CH_2O)_n$ wherein n is an integer of 2-4000. The PEG includes various terminal groups for PEGylation, and thus the PEG may be covalently bound to a terminal amine group, a terminal cysteine, or a carboxyl group of the FUD via a carbonyl, amide, urethane, secondary amine, thioether, disulfide, thiol or hydrazone. In an aspect, FUD can be modified to contain a terminal Cys residue allowing for thioether bond formation through a Michael's addition between a thiol group of a cysteine residue and a double bond of a maleimide ring functionality located on the PEG.

The PEG used in the PEGylation can have a molecular weight of about 2-50 kDa, 5-50 kDa, or 10-40 kDa.

According to an embodiment, the PEGylation of FUD is a mono-end-PEGylation. The term "mono-end-PEGylation" refers to the conjugation of a single molecule of PEG to the N-terminus or C-terminus of FUD. In an aspect, the PEGylated FUD is N-terminal PEGylated FUD.

The PEGylated FUD can be formed by conjugating FUD and an activated PEG. Activated PEG can be represented by the formula PEG-A, wherein (A) contains a reactive group which can react with an amino, imino, or thiol group on an amino acid residue of a peptide or a linker moiety covalently attached to the peptide.

An example of a useful activated PEG is a PEG-aldehyde compound (e.g., a methoxy PEG-aldehyde), such as methoxy PEG-propionaldehyde, and a PEG-maleimide compound, such as methoxy PEG-maleimide. Examples of PEGs that can be used in N-terminal PEGylation include, for example, PEGs manufactured by Jenken Technology USA such as: Y-shape PEG aldehyde, Y-shape PEG acetaldehyde, Y-shape PEG propionaldehyde, methoxy PEG propionaldehyde, and the like.

N-terminal PEGylation with methoxy PEG-propionaldehyde can be achieved by reductive alkylation in the presence of $NaCNBH_3$. PEGylation of an N-terminal Cysteine residue with a methoxy PEG maleimide can be achieved by specific reaction of the maleimide double bond with a reduced sulfhydryl group of the Cysteine residue in weakly basic or weakly acidic conditions.

In an embodiment, the mono-end PEGylated FUD comprises a detectable label. Exemplary detectable labels include imaging agents such as radionuclides, fluorophores such as fluorescein, rhodamine, Texas Red, Cy2, Cy3, Cy5, and the AlexaFluor® (Invitrogen, Carlsbad, Calif.) range of fluorophores, antibodies, gadolinium, gold, nanomaterials, horseradish peroxidase, alkaline phosphatase, derivatives thereof, and mixtures thereof.

As used herein, "pharmaceutical composition" means therapeutically effective amounts of the mono-end-PEGylated FUD together with a pharmaceutically acceptable excipient, such as diluents, preservatives, solubilizers, emulsifiers, and adjuvants. As used herein "pharmaceutically acceptable excipients" are well known to those skilled in the art.

Pharmaceutical compositions include reconstitutable powders, elixirs, liquids, solutions, suspensions, emulsions, powders, granules, particles, microparticles, dispersible granules, cachets, inhalants, aerosol inhalants, patches, particle inhalants, implants, depot implants, injectables (including subcutaneous, intramuscular, intravenous, and intradermal), infusions, and combinations thereof.

In one embodiment, the pharmaceutically acceptable excipient is suitable for parenteral administration. Alternatively, the pharmaceutically acceptable excipient can be suitable for subcutaneous, intravenous, intraperitoneal, intramuscular, or sublingual administration. Pharmaceutically acceptable excipients include sterile aqueous solutions or dispersions and sterile powders for the extemporaneous preparation of sterile injectable solutions or dispersions. The use of such media and agents for pharmaceutically active substances is well known in the art.

Parenteral pharmaceutical compositions are typically sterile and stable under the conditions of manufacture and storage. The pharmaceutical composition may be in lyophilized form. The composition can be formulated as a solution, microemulsion, liposome, or other ordered structure suitable to high drug concentration. The excipient can be a solvent or dispersion medium containing, for example, water, ethanol, polyol (for example, glycerol, propylene glycol, and liquid polyethylene glycol), and mixtures thereof. A stabilizer can be included in the pharmaceutical composition.

Pharmaceutical compositions can include isotonic agents, for example, sugars, polyalcohols such as mannitol, sorbitol, or sodium chloride. Prolonged absorption of the injectable compositions can be brought about by including in the composition an agent which delays absorption, for example, monostearate salts and gelatin. The mono-end-PEGylated FUD can be formulated in a time release formulation, for example in a composition which includes a slow release polymer. The mono-end-PEGylated FUD can be prepared with carriers that will protect the compound against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polylactic acid and polylactic, polyglycolic copolymers (PLG). Many methods for the preparation of such formulations are known to those skilled in the art.

The mono-end-PEGylated FUD may be administered parenterally in a sterile medium, either subcutaneously, or intravenously, or intramuscularly, or intrasternally, or by infusion techniques, in the form of sterile injectable aqueous or oleaginous suspensions. Depending on the vehicle and concentration used, the mono-end-PEGylated FUD can either be suspended or dissolved in the vehicle. Advantageously, adjuvants such as a local anaesthetic, preservative and buffering agents can be dissolved in the vehicle. Subcutaneous administration can be daily administration.

Formulations for pulmonary administration include aerosol formulations and dry powder formulations. Excipients for aerosol administration include carbohydrates, amino acids, polypeptides, lipids, buffers, salts, polyalcohols, and mixtures thereof. Specific excipients for aerosol administration include galactose, mannose, sorbose, lactose, glucose, trehalose, raffinose, maltodextrins, dextrans, mannitol, xylitol, alanine, glycine, tryptophan, tyrosine, leucine, phenylalanine, oleates, stearates, myristates, alkylethers, alkyl arylethers, sorbates, polyvinylpyrrolidone (PVP), 1,1,1,2-tetrafluoroethane (P134a), 1,1,1,2,3,3,3-heptafluoro-n propane (P227), 2H, 3H-perfluoropentane (HPFP) and mixtures comprising at least one of the foregoing. Excipients for dry powder formulations include lactose, glucose, or a mixture of lactose and glucose.

Pharmaceutical compositions may conveniently be presented in unit dosage form and may be prepared by any of the methods well known in the art of pharmacy. The term "unit dosage" or "unit dose" means a predetermined amount of the active ingredient sufficient to be effective for treating an indicated activity or condition. Making each type of pharmaceutical composition includes the step of bringing the active compound into association with a carrier and one or more optional accessory ingredients. In general, the formulations are prepared by uniformly and intimately bringing the active compound into association with a liquid or solid carrier and then, if necessary, shaping the product into the desired unit dosage form.

In an aspect, a pharmaceutical composition can further comprise a second active agent such as an anti-fibrotic agent, an anti-cancer agent, or a combination thereof, as described below.

The mono-end-PEGylated FUD is particularly useful in the inhibition of fibrosis in subjects in need thereof, particularly organ fibrosis. Fibrosis is the scarring process that occurs in organs, destroying the normal organ architecture, leading to loss of normal organ tissue and replacement with scar tissue. Fibrosis is a major pathological factor in diseases of the liver, lung, heart, skin, pancreas, muscle, brain, intestine, eyes, bone marrow and large vessels. As an example, in the kidney, many diseases that trigger tissue damage lead ultimately to a progressive disease known as chronic kidney disease (CKD). Therapeutically effective amounts of the mono-end-PEGylated FUD can be determined by one of ordinary skill in the art, and includes up to 50 mg/kg, such as 1 to 50 mg/kg or 1-12.5 mg/kg, preferably daily.

Approximately 30 million people in the U.S. suffer from some level of chronic kidney disease. The therapeutic interventions, such as medications that decrease blood pressure, are not entirely effective as approximately 660,000 patients develop End Stage Renal Disease (ESRD). Dialysis and transplantation are treatment options for ESRD but only about 17% of those in need receive a transplant and the 5-10 year mortality rate for dialysis patients is approximately 65%. Following transplantation, there is a 5 and 10 year graft failure rate of approximately 30% and 50%, respectively. There is thus a great need for new treatments for chronic kidney disease, particularly chronic kidney disease associated with kidney disease or kidney transplant.

Diseases or conditions that can be ameliorated by administering mono-end-PEGylated FUD include, without limitation, CKD which can be related to, without limitation, diabetes mellitus, hypertension, arteriosclerosis, atherosclerosis, autoimmune diseases including, without limitation, lupus, anti-neutrophil cytoplasmic antibody (ANCA)-associated vasculitis, anti-glomerular basement membrane (GBM) disease, other glomerular diseases including focal segmental glomerular sclerosis (FSGS), IgA nephropathy, membranous nephropathy, genetic diseases including, without limitation, Alports Syndrome, polycystic kidney disease, kidney infections including urinary tract infections (UTIs), viral or bacterial or parasite-related kidney disease, or CKD following xenobiotic exposure, sepsis or ischemic injuries; fibrosing lung diseases including, without limitation, idiopathic pulmonary fibrosis (IPF), chronic obstructive pulmonary disease (COPD), or asthma; fibrosing skin diseases including, without limitation, scleroderma; fibrosing heart diseases including, without limitation, ischemic cardiomyopathy and post myocardial infarction cardiac failure; fibrosing muscle diseases; fibrosing brain diseases including, without limitation, fibrosis of the brain following stroke; fibrosing gut diseases including, without limitation, associated with Crohns Colitis or other diseases with strictures; fibrosis of the peritoneum, as occurs in, without limitation, post-surgical laparotomies; and fibrosis of the pancreas as occurs, without limitation, following pancreatitis.

Specific organ fibrosis diseases include interstitial fibrosis, glomerulosclerosis, liver fibrosis, pulmonary fibrosis, peritoneum fibrosis, myocardial fibrosis, dermatofibrosis, post-surgery adhesions, benign prostatic hypertrophy, skeletal muscle fibrosis, dermatosclerosis, multiple sclerosis, pancreatic fibrosis, liver cirrhosis, myosarcoma, neurofibroma, pulmonary interstitial fibrosis, diabetic nephropathy, Alzheimer's disease or vascular fibrosis.

Inhibiting fibrosis refers to inhibiting the full development of fibrosis, which is associated with diminished organ function such as in the case of lung, kidney, heart, liver, pancreas and skin. Inhibiting fibrosis refers to lessening symptoms of a fibrosis, such as the formation of scar tissue or an increase in range of motion or a decrease in pain. "Treatment" refers to a therapeutic intervention that ameliorates a sign or symptom of a disease or pathological condition related to the disease, such as the fibrosis associated with a disease or pathological condition.

In an aspect, the method of treating organ fibrosis can further comprise administering a second therapeutic agent for the treatment of organ fibrosis. Exemplary second therapeutic agents for the treatment of organ fibrosis include pirfenidone, nintedanib, ACE inhibitors such as enalapril. Rho inhibitors such as fasudil, and AT1-receptor inhibitors such as losartan and atrasentan.

In another aspect, the fibrosis is associated with cancer. The progression of solid tumors is associated with changes in the extracellular matrix (ECM). These changes in the ECM disrupt cell polarity and stimulate cell proliferation, creating a context for cancer formation and development. The presence of fibrotic lesions can increase the risk of cancer in many tissues such as the ovary, pancreas and breast. Fibrosis is also associated with cancers such as multiple myeloma. Thus, administering mono-end-PEGylated FUD in a patient with cancer or a patient suspected of having cancer can decrease fibrosis and potentially slow the progression of disease, in particular the progression of metastasis.

Exemplary anti-cancer agents for co-administration with PEG-FUD include acivicin, aclarubicin, acodazole, acronine, adozelesin, aldesleukin, alitretinoin, allopurinol, altretamine, ambomycin, ametantrone, amifostine, aminoglutethimide, amsacrine, anastrozole, anthramycin, arsenic trioxide, asparaginase, asperlin, azacitidine, azetepa, azotomycin, batimastat, benzodepa, bicalutamide, bisantrene, bisnafide dimesylate, bizelesin, bleomycin, brequinar, bropirimine, busulfan, cactinomycin, calusterone, capecitabine, caracemide, carbetimer, carboplatin, carmustine, carubicin, carzelesin, cedefingol, celecoxib, chlorambucil, cirolemycin, cisplatin, cladribine, crisnatol mesylate, cyclophosphamide, cytarabine, dacarbazine, dactinomycin, daunorubicin, decitabine, dexormaplatin, dezaguanine, dezaguanine mesylate, diaziquone, docetaxel, doxorubicin, droloxifene, dromostanolone, duazomycin, edatrexate, eflornithine, elsamitrucin, enloplatin, enpromate, epipropidine, epirubicin, erbulozole, esorubicin, estramustine, etanidazole, etoposide, etoprine, fadrozole, fazarabine, fenretinide, floxuridine, fludarabine, fluorouracil, flurocitabine, fosquidone, fostriecin, fulvestrant, gemcitabine, hydroxyurea, idarubicin, ifosfamide, ilmofosine, interleukin II (IL-2, including recombinant interleukin II or rIL2), interferon alfa-2a, interferon alfa-2b, interferon alfa-n1, interferon alfa-n3, interferon beta-Ia, interferon gamma-Ib, iproplatin, irinotecan, lanreotide, letrozole, leuprolide, liarozole, lometrexol, lomustine, losoxantrone, masoprocol, maytansine, mechlorethamine hydrochloride, megestrol, melengestrol acetate, melphalan, menogaril, mercaptopurine, methotrexate, metoprine, meturedepa, mitindomide, mitocarcin, mitocromin, mitogillin, mitomalcin, mitomycin, mitosper, mitotane, mitoxantrone, mycophenolic acid, nelarabine, nocodazole, nogalamycin, ormnaplatin, oxisuran, paclitaxel, pegaspargase, peliomycin, pentamustine, peplomycin, perfosfamide, pipobroman, piposulfan, piroxantrone hydrochloride, plicamycin, plomestane, porfimer, porfiromycin, prednimustine, procarbazine, puromycin, pyrazofurin, riboprine, rogletimide, safingol, semustine, simtrazene, sparfosate, sparsomycin, spirogermanium, spiromustine, spiroplatin, streptonigrin, streptozocin, sulofenur, talisomycin, tamoxifen, tecogalan, tegafur, teloxantrone, temoporfin, teniposide, teroxirone, testolactone, thiamiprine, thioguanine, thiotepa, tiazofurin, tirapazamine, topotecan, toremifene, trestolone, triciribine, trimetrexate, triptorelin, tubulozole, uracil mustard, uredepa, vapreotide, verteporfin, vinblastine, vincristine sulfate, vindesine, vinepidine, vinglycinate, vinleurosine, vinorelbine, vinrosidine, vinzolidine, vorozole, zeniplatin, zinostatin, zoledronate, zorubicin, and combinations comprising at least one of the foregoing. In an aspect, co-administration of an anti-cancer agent with PEG-FUD provides for a reduction in the dosage of the anti-cancer agent.

In an aspect, the PEG-FUD is used in the treatment of idiopathic pulmonary fibrosis. Idiopathic Pulmonary Fibrosis (IPF) is a devastating disorder that leads to the death of over 40,000 individuals in the U.S. each year. Tens of thousands more are faced with shortness of breath, and a diminished ability to exercise and carry on daily activities due to decreased lung function. Patients face a dismal prognosis; untreated IPF leads to death in about 4 years. Unfortunately, there are few effective treatments for IPF, none of which completely halt progression of fibrosis. Fibrosis of the lung is due to inexorable deposition of extracellular matrix (ECM). ECM deposition requires formation of a nascent fibronectin matrix that serves as a scaffold for incorporation of other ECM proteins, such as collagens, and, thereby, fibrosis. In an embodiment, treatment of IPF comprises subcutaneous administration of PEG-FUD.

In another embodiment, labeled PEG-FUD, e.g., fluorescently labeled PEG-FUD, is used as a probe for areas of injured and repairing tissue, such as that seen in active pulmonary (or other organ) fibrosis, as well as to identify clot formation and wound healing.

Thus, a method of probing for injured or repairing tissue in an individual in need thereof, comprising administering to the individual a diagnostic amount of the mono-end-PEGylated FUD described herein. Diagnostic amounts of the mono-end-PEGylated FUD can be determined by one of ordinary skill in the art, and include up to 1 or 5 mg/kg, such as 0.5-1 mg/kg.

As used herein, a "subject" includes mammals, specifically humans.

The invention is further illustrated by the following non-limiting examples.

EXAMPLES

Methods: Synthesis and Characterization of PEGylated FUD

FUD and mFUD Synthesis: The FUD peptide and its mFUD control peptide variant were recombinantly expressed in BL21 (DE3) *E. Coli* as a His-tagged pET-ELMER construct using previously described protocol with modifications recently reported in the art pertaining to His-tag removal. Briefly, expression of FUD or mFUD was induced by 1 mM isopropyl β-D-1thiogalactopyranoside and cell lysis was facilitated by a lysis buffer (100 mM sodium phosphate, 10 mM Tris, 8M urea, 5 mM imidazole, pH 8.0). The lysate was cleared of particulates via centrifugation and incubated overnight with Ni-NTA agarose (Qiagen). The Ni-NTA agarose was washed three times with a washing buffer (100 mM sodium phosphate, 10 mM Tris, 8M urea, 5 mM imidazole, pH 8.0) and three more times with an elution buffer (20 mM Tris, 150 mM NaCl, 2.5 mM $CaCl_2$, pH 8.4). Elution of FUD and removal of the His tag was achieved by using a thrombin cleavage site between the His-tag and FUD. For this, FUD bound to the Ni-NTA agarose was incubated with 1 unit of Bovine α-Thrombin per 1 mg of expressed peptide. The peptide was further purified via fast protein liquid chromatography (FPLC) using HiTrap™ Q HP column as described in the PEG-FUD Purification section. Peptide identity was verified via UPLC-ESI ultra high resolution QTOF MS. The concentration of FUD and PEG-FUD conjugates were obtained with absorbance measurements at 280 nm using ε=0.496 as described in the art. The concentration of mFUD was determined similarly using ε=0.744.

Preparation of PEGylated FUD and mFUD: PEGylation and subsequent FPLC purification were carried out using the same procedure for all constructs. The FUD or mFUD peptide was incubated with 10 kDa and 20 kDa linear or 40 kDa branched methoxy-PEG propionaldehyde (NOF, Japan) in 50 mM sodium acetate buffer (pH 5.5). All materials were dissolved in or exchanged via dialysis into the appropriate buffer prior to mixing. The reaction was carried out in the presence of 26.7 mM $NaCNBH_3$ for 16 hrs at 4° C. Final FUD peptide concentration of 0.63 mg/mL was used with a FUD:PEG molar ratio of 1:10. The polydispersity of the PEG reagent was 1.04, 1.02, and 1.06 for 10 kDa, 20 kDa, and 40 kDa PEG, respectively. After 16 hr reaction time, the reducing agent was removed via dialysis in 50 mM sodium acetate buffer (pH 5.5). The buffer was switched after 1 and 4 hours, and then exchanged for 20 mM Tris (pH 8.0) for 3 more hrs.

FPLC Separation and Purification of PEGylated FUD and mFUD: The PEG-FUD or PEG-mFUD reaction mixture was loaded onto a HiTrap™ Q HP anion exchange column (GE Healthcare Life Sciences, USA) initially equilibrated with Buffer A (20 mM Tris, pH 8.0). Upon sample injection, the column was washed with 2 CVs of Buffer A and the sample was eluted with a 10 CV gradient of Buffer B (1 M NaCl in 20 mM Tris, pH 8.0) at a flow rate of 3.5 mL/min. The fraction containing PEG-FUD was collected, concentrated using Amicon® Ultra-15 3000 MWCO Centrifugal Filter Units (MilliporeSigma), and snap frozen. Routine purity assessment was carried out using RP-HPLC.

GPC Characterization: FUD and 10 kDa, 20 kDa, and 40 kDa PEG-FUD were loaded onto a TSKgel® $G4000PW_{XL}$ Column (TOSOH Bioscience) connected to a 1100 Series (Agilent) system and equilibrated and eluted with 10 mM Phosphate Buffer (pH 7.4) at a flow rate of 1 mL/min. A typical run was allowed to proceed for 30 minutes. A DAD detector set to 280 nm was used to detect the peptides.

HPLC Characterization: Purified FUD and 10 kDa, 20 kDa, and 40 kDa PEG-FUD peptides were loaded onto a Zorbax SB-C8 4.6×75 mm column with a 3.5 μm pore size (Agilent) connected to a Prominence UFLC system (Shimadzu). A water/acetonitrile elution gradient with a flow rate of 1 mL/min was used to separate the sample. A typical run was allowed to proceed for 46 minutes. Absorbance at 280 nm was used to detect the peptides.

Matrix-assisted laser desorption/ionization—time of flight (MALDI-TOF) Characterization of PEG-FUD: Prior to analysis, the peptide complexes were dialyzed overnight into deionized $H_2O$ using a 3000 MWCO dialysis membrane. The samples were then purified on Omix C18 Tips according to the manufacturer's protocol (Agilent). Purified PEGylated peptides were then mixed 1:1 with 10 mg/mL α-cyano-4-hydroxycinnamic acid (1 μL analyte and matrix) and analyzed on UltraFleXtreme MALDI-TOF (Broker) spectrometer in positive ion, linear mode.

Isothermal Titration calorimetry (ITC): ITC experiments were performed using a VP-ITC microcalorimeter (MicroCal, LLC) with a cell volume of 2.2 mL. In a typical experiment, the cell was filled with 1.4 mL of 2 μM human plasma FN and the syringe was filled with 1 mL of 28 μM FUD or PEG-FUD peptides. The temperature was set to 25° C. The titration experiment was performed in 39 injections (1×1, 4×4, and 34×8 μL) delivered in 120 sec intervals. Prior to injection, both FN and the peptides were dialyzed in separate dialysis bags overnight into the same PBS buffer (pH 7.4) solution. Routine analysis involved discarding of the first data point and subtraction of peptide into PBS buffer control run. Data were fit using one set of sites model Lavenberg-Marquardt nonlinear regression in Origin 7.0.

Matrix Assembly Assay: The matrix assembly assay was conducted in the 96-well plate format as described in the art. AH1F human skin fibroblast cells resuspended in 2% fetal bovine serum were added to each well for a density of 60,000 cells per well. A 1 hr incubation period at 37° C. followed to allow cell adhesion and spreading. FUD, PEG-FUD, or PEG-mFUD were added to each well following incubation. Immediately, Alexa Fluor® 488 fluorescence labeled human plasma fibronectin (A488-FN) was then added to each well for a final FN concentration of 11 μg/mL. The cells were then incubated for 24 hours at 37° C. Non-assembled FN was removed from each well by washing with Hank's Balanced Salt Solution (HBSS) containing $Ca^{2+}$ and $Mg^{2+}$. The well volume was restored to 60 μL with HBSS and a fluorescence reading from the bottom of each well was taken using a Synergy™ H1 (Biotek) plate reader (excitation: 485 nm, Emission: 538 nm). Cell viability was quantified using CellTiter-Glo® cell viability assay using the manufacturer's protocol. A 30 μL aliquot of HBSS was removed from each well and was replaced with 30 μL of the luminescence reagent prepared shortly beforehand. Luminescence was quantified using the same plate reader. The average of fluorescence values of a no A488FN or inhibitor control group were routinely subtracted from the readings of each well and were normalized using each well's corresponding luminescence value. Lastly, the cell viability normalized fluorescence values were expressed as a percentage of the 0 nM drug control group. The final results were processed using Graphpad Prism 7.0 software. IC50 values were extracted using a four-parameter dose-response curve function. Student's t test was used to determine significance of differences among peptides at a given drug concentration.

Example 1: PEG-FUD Synthesis

The FUD peptide and a mutated FUD control peptide, termed mFUD, were successfully expressed using recombinant technology. Peptide expression was induced using IPTG at a colony optical density of 0.6, approximately 4 hours following colony seeding. In a typical experiment, a 6 L batch was created to recover 8 mg of FUD or 3 mg of mFUD per liter of cell culture medium. Ion exchange chromatography was used as the final purification step following Ni-NTA agarose His-tag purification. A singular peak corresponding to the FUD or mFUD peptide eluted at 33.0% B and 33.3% B, respectively, when an anionic exchanger was used (data not shown). The isolate identity was verified using LC-MS, agreeing with the theoretical mass of the FUD peptide (6003.820025 Da) within 1.4 ppm mass accuracy and within 0.15 ppm mass accuracy for the mFUD peptide (6024.78754 Da).

Figure 2:
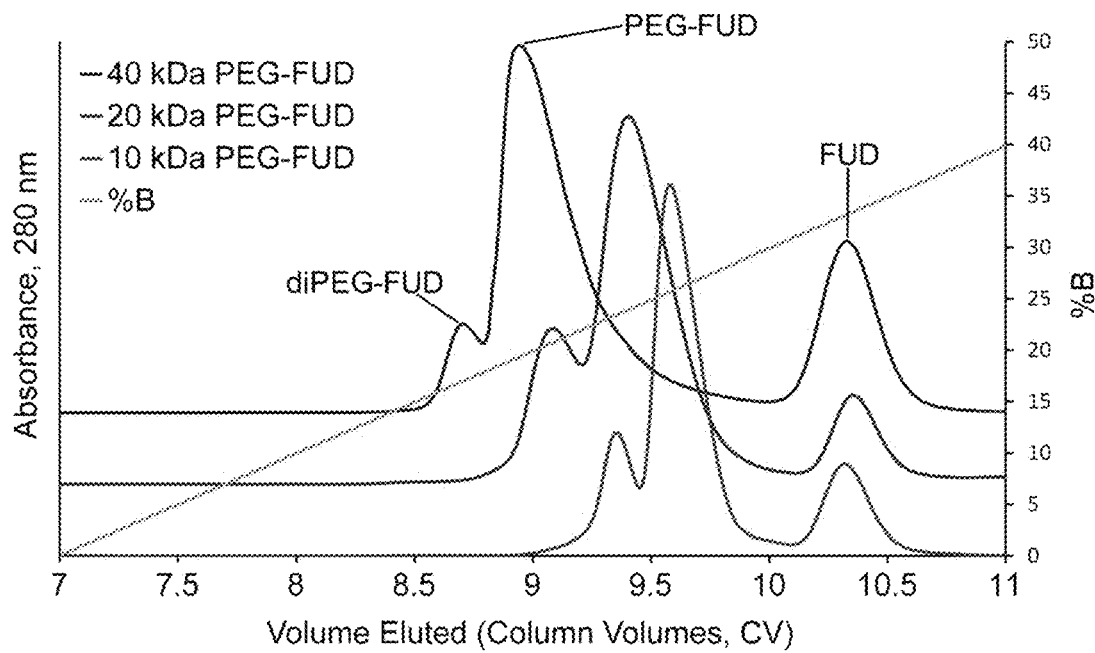
FIG. 2 shows an FPLC ion exchange chromatogram demonstrating isolation by fractionation of the 10 kDa, 20 kDa, and 40 kDa PEG-FUD constructs. An anionic exchanger combined with a mobile phase gradient of 20 mM Tris A side and 1 M NaCl B side were used to elute the peptide and separate it from unreacted FUD, PEG, and diPEGylated species.

The 10 kDa, 20 kDa, and 40 kDa PEGylated FUD constructs were synthesized using reductive addition chemistry (FIG. 1) shown previously to be N-terminus specific using proteolytic digests in tandem with HPLC and/or MALDI-TOF analysis. This reaction chemistry targets primary amines present in the peptide to covalently attach a PEG moiety via its aldehyde functionality. The more reactive α-amino group of the N-terminal residue of the peptide is preferentially targeted at low pH in this reaction strategy because of its lower $pK_a$ (7.6-8.0) compared to other amines present in the peptides, including ∉-amino groups of Lys residues (10.0-10.2). After reaction time optimization, a 16 hour method was chosen for most efficient production of PEG-FUD constructs, selecting for a maximal FPLC PEG-FUD peak height. As shown in FIG. 2, the generated 10 kDa, 20 kDa, and 40 kDa PEG-FUD final conjugates eluted at 25.8% B, 23.8% B and 19.6% B, respectively, upon ion exchange chromatography purification and were separated from unreacted FUD, PEG, and other species by fractionation.

In addition to synthesizing a set of PEG-FUD peptide variants, the mFUD control peptide was also PEGylated using 20 kDa methoxy-PEG propionaldehyde to function as a control peptide for in vitro efficacy experiments. The same procedure was used to create this construct as with all PEG-FUD variants. A similar reaction species distribution and anion exchange elution profile was observed between 20 kDa PEG-mFUD and 20 kDa PEG-FUD. Analysis via RP-HPLC revealed the retention time of mFUD increasing from 13.259 min to 21.988 min upon PEGylation with 20 kDa PEG (data not shown). This retention time compares to 21.984 min of the 20 kDa PEG-FUD conjugate.

Example 2: Characterization of PEG-FUD

Figure 3:
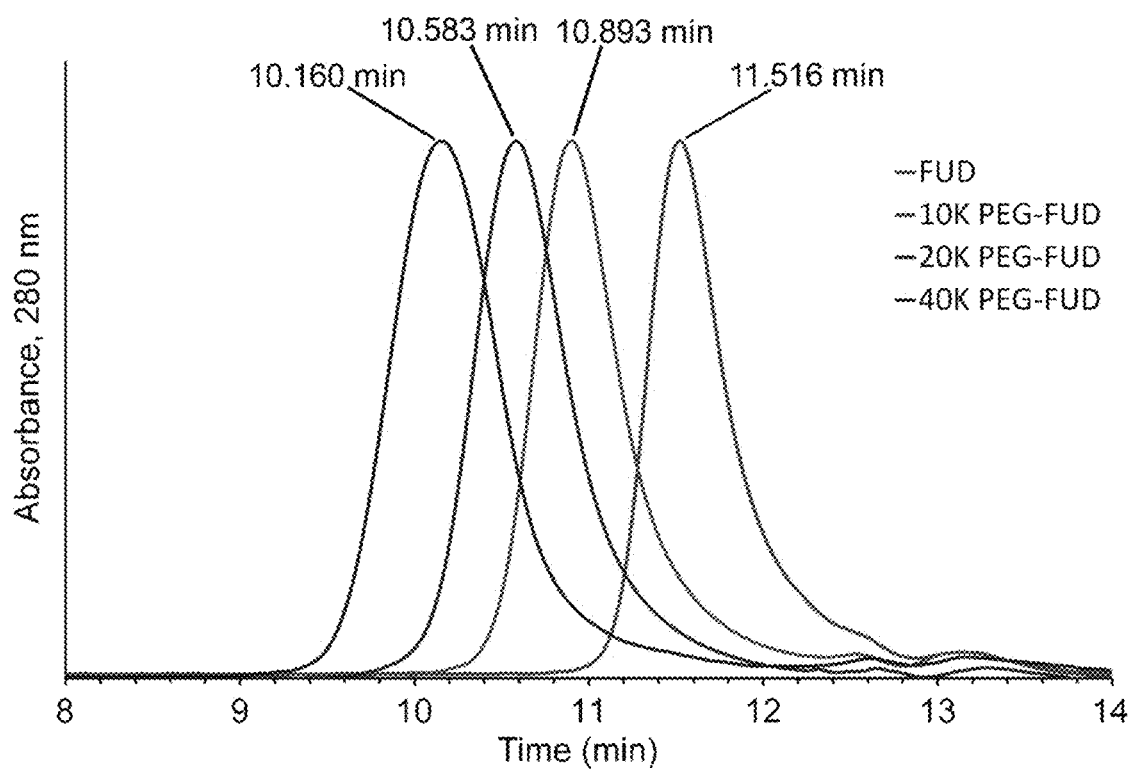
FIG. 3 shows that Gel Permeation Chromatography (GPC) experiments reveal reduced 10 kDa, 20 kDa, and 40 kDa PEG-FUD retention times and suggest increase in molecular weight of FUD upon PEGylation. Experiments were done using 10 mM pH 7.4 Phosphate Buffer mobile phase.
Figure 4:
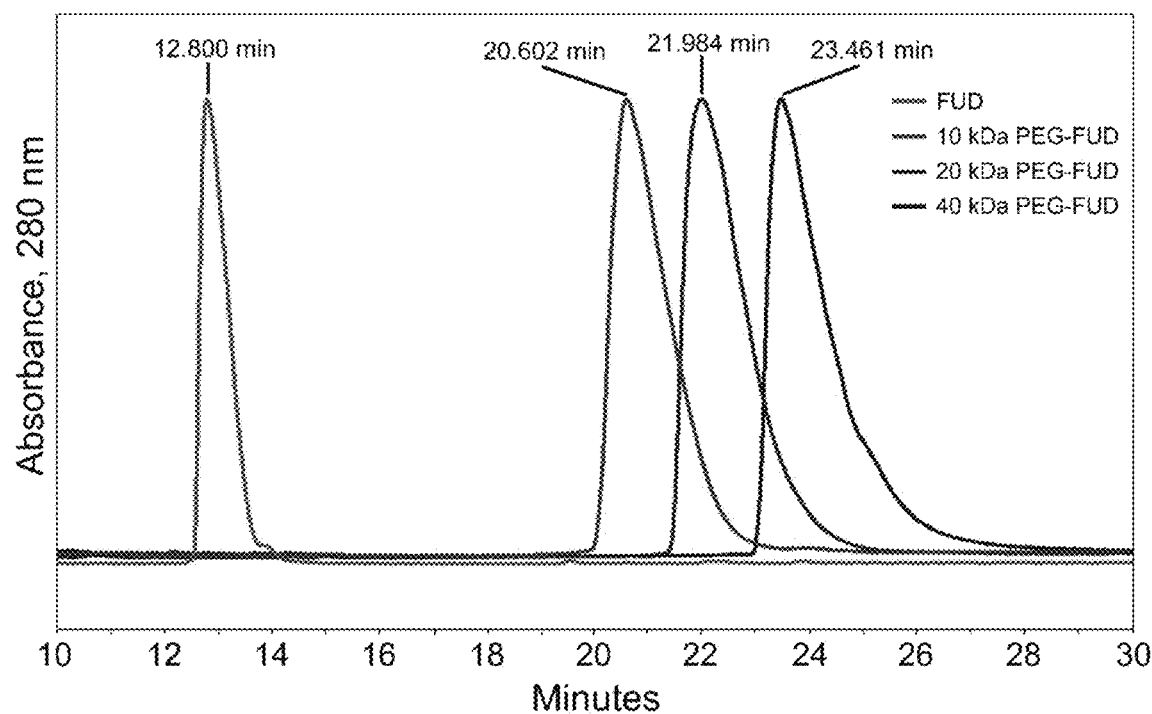
FIG. 4 shows a Reversed Phase High Performance Liquid Chromatography (RP-HPLC) chromatograph showing an increase of FUD retention time after PEGylation. The analysis was made using a C8 column combined with an A side $H_2O$ and B side acetonitrile mobile phase elution gradient.

Gel Permeation Chromatography (GPC) and Reversed Phase High Performance Liquid Chromatography (RP-HPLC) analysis yielded singular peaks for each PEG-FUD construct, confirming sample purity, with shifted retention times and peak broadening characteristic of conjugation with a polydisperse PEG polymer. Upon attachment of a PEG moiety, the GPC analysis retention time of FUD decreased from 11.516 min to 10.893 min, 10.583 min, and 10.160 min for 10 kDa, 20 kDa, and 40 kDa PEG-FUD, respectively (FIG. 3). RP-HPLC analysis yielded a FUD retention time increase from 12.800 min to 20.602 min, 21.984 min, and 23.461 min for 10 kDa, 20 kDa, and 40 kDa PEGylated conjugates, respectively (FIG. 4). Together, the two analytical techniques suggest covalent modification of FUD with a PEG moiety. The degree of PEGylation of the three PEG-FUD conjugates was verified using Matrix-Assisted Laser Desorption/Ionization Mass Spectrometry (MALDI-MS).

Figure 5:
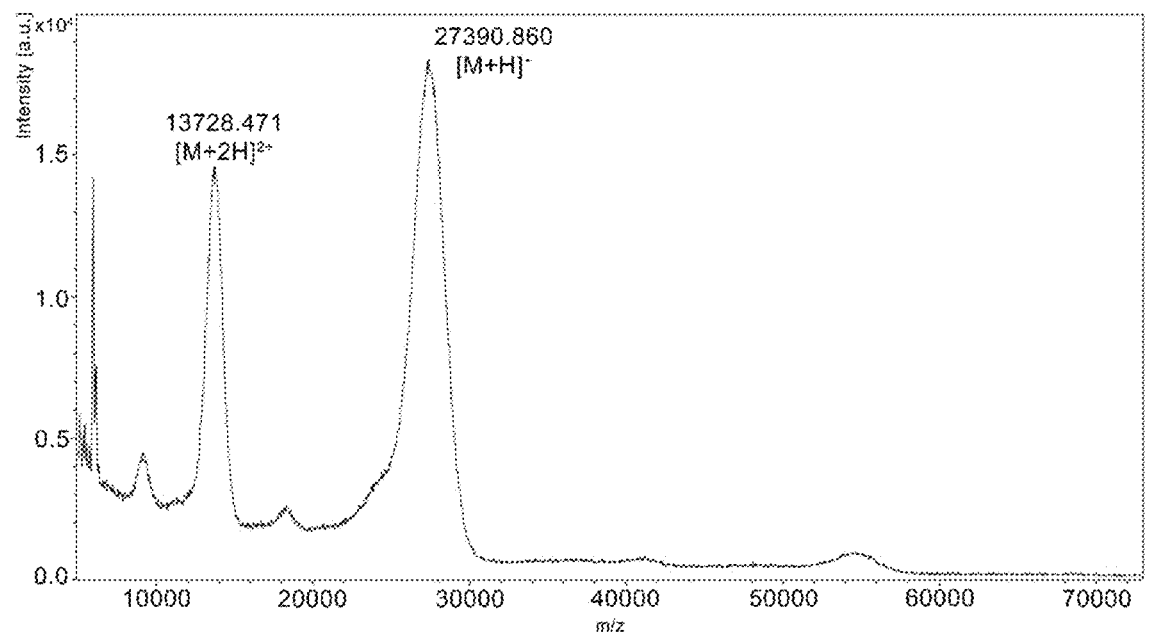
FIG. 5 shows a MALDI-TOF spectrum verifying the molecular weight of the 20 kDa PEG-FUD construct. A 6 kDa FUD reacted with a single 21.3 kDa nominal MW PEG yielded 27.3 kDa PEG-FUD. The analysis was made using α-cyano-4-hydroxycinnamic acid matrix.

The nominal molecular weight of the 20 kDa PEG-FUD conjugate was determined to be 27,390 Da using this technique (FIG. 5). This weight corresponds to attachment of one PEG unit (21,304 Da) to the FUD peptide (6,004 Da). The mass of the PEG-FUD conjugates generated with 10 kDa and 40 kDa PEG was similarly characterized. The nominal molecular weights of the 10 kDa and 40 kDa PEG-FUD constructs were determined to be 16,946 Da and 49,582 Da, respectively, corresponding to attachment of one PEG unit (11,096 Da and 43,667 Da) to the FUD peptide (data not shown). This technique was also used to ascertain the mass of the PEG-mFUD conjugate (data not shown). As expected, a nominal mass of 27,400 Da was observed.

Together, the GPC, RP-HPLC, and MALDI-TOF data demonstrate successful synthesis and isolation of the PEG-FUD and PEG-mFUD peptides.

Example 3: PEG-FUD Binding Studies

Figure 6:
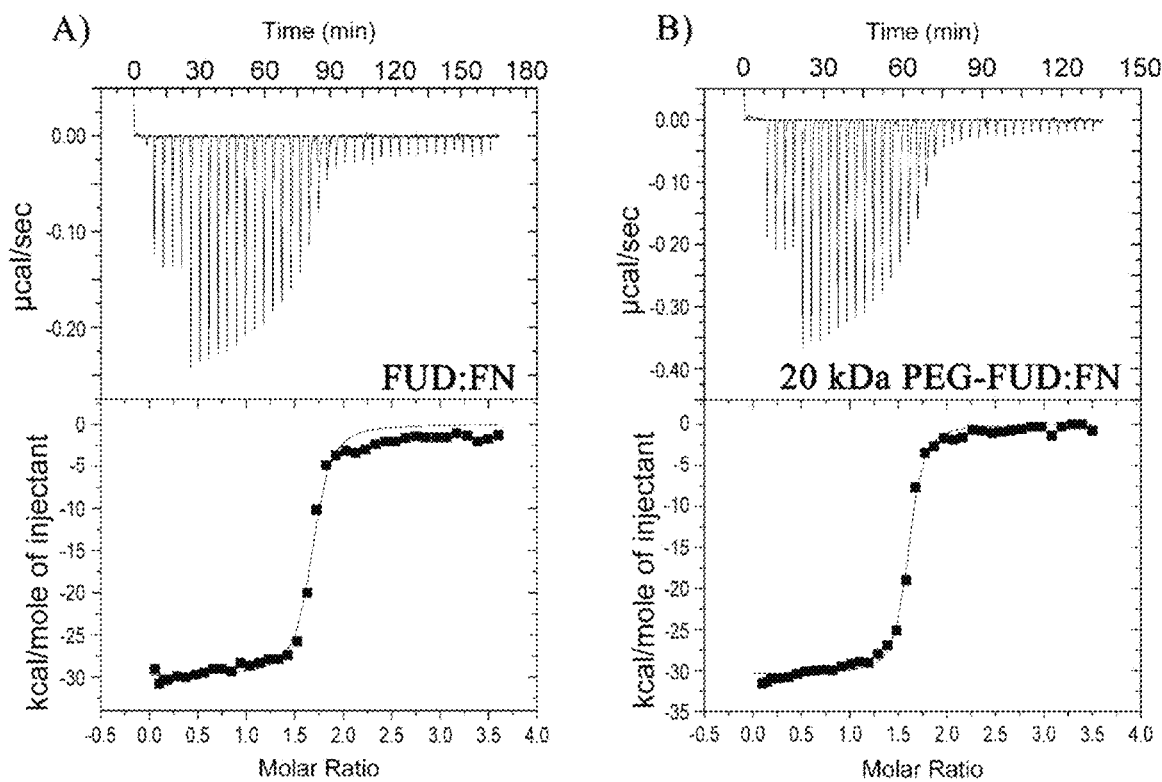
FIG. 6 shows determination of binding affinity ($K_d$) and other thermodynamic parameters using Isothermal Titration calorimetry (ITC). All experiments were performed using pH 7.4 PBS, 25° C. chamber conditions, and human plasma FN. A) FUD into FN and B) 20 kDa PEG-FUD into FN experiment sample isotherm and thermograph. Each experiment was repeated in triplicates.
Figure 7:
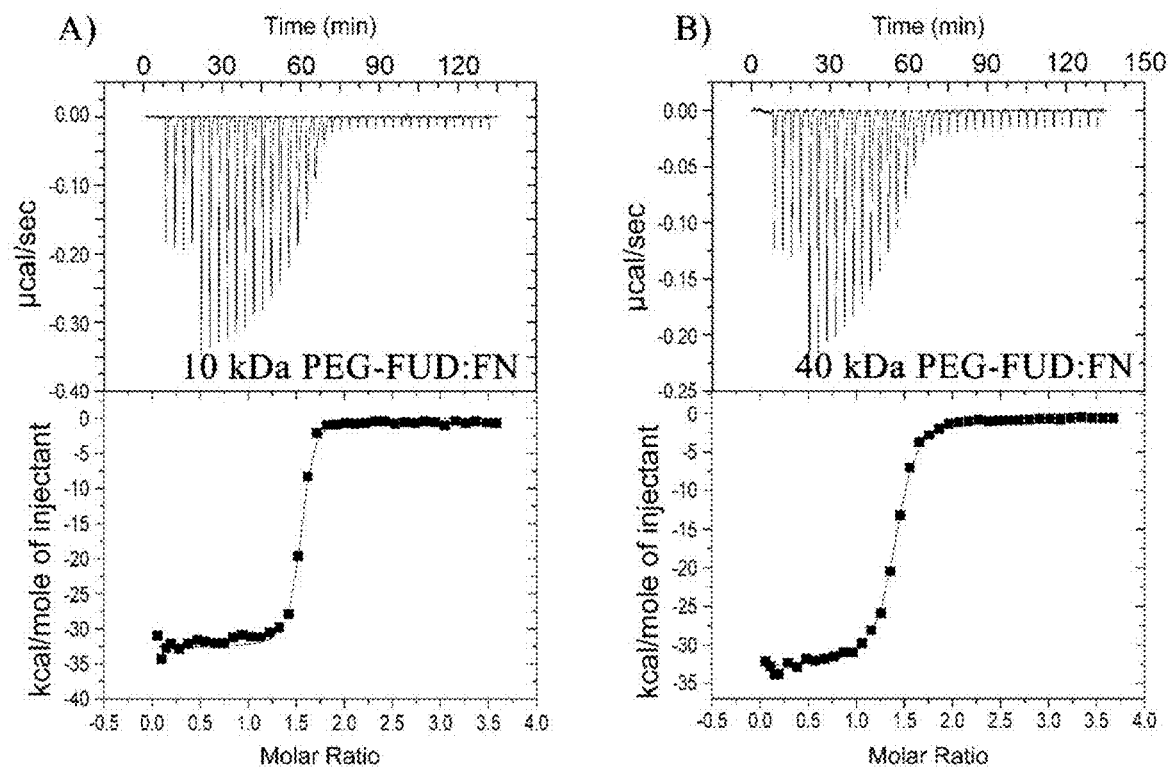
FIG. 7 shows the determination of binding affinity ($K_d$) and other thermodynamic parameters using Isothermal Titration calorimetry (ITC). All experiments were performed using pH 7.4 PBS, 25° C. chamber conditions, and human plasma FN. A) 10 kDa PEG-FUD into FN and B) 40 kDa PEG-FUD into FN experiment sample isotherm and thermograph. Each experiment was repeated in triplicates.

The binding of 10 kDa, 20 kDa, and 40 kDa PEG-FUD to FN was studied using Isothermal Titration calorimetry (ITC). This technique was used to determine the thermodynamic parameters as well as the binding constant ($K_d$) of the interaction. The peptide was injected into a human plasma FN solution in PBS at pH 7.4 and 25° C. in triplicate runs. Sample FUD and 20 kDa PEG-FUD into fibronectin ITC isotherms and thermographs are presented in FIG. 6. TC results of additional conjugates are shown in FIG. 7. The overall thermodynamic binding parameters are summarized and presented in Table I. Similar binding affinity and binding parameters were observed for both the peptide and its PEGylated constructs. A $K_d$ of 6 (±3) nM was detected for FUD:FN. Similarly, a $K_d$ of 4.6 (±0.5) nM was detected for 10 kDa PEG-FUD:FN, 10 (±2) nM for 20 kDa PEG-FUD:FN, and 14.7 (±0.9) nM for 40 kDa PEG-FUD:FN interactions. Similar entropy change of −65 (±3) cal/mol, −74 (±7) cal/mol, −66 (±7) cal/mol, and −73 (±2) and enthalpy change of −31 (±1) kcal/mol, −34 (±2) kcal/mol, −30 (±1) kcal/mol, and −32.5 (±0.5) kcal/mol were detected for the interaction of FUD and 10 kDa, 20 kDa, and 40 kDa PEG-FUD with FN, respectively. Together, these findings indicate that the tight nanomolar binding affinity as well as the overall interaction of FUD for FN is not significantly affected by N-terminal covalent attachment with a PEG moiety. This observation is contrary to the expectation of PEG attachment diminishing a drug's affinity for its binding partner and presents an unexpected but desired feature of the PEG-FUD peptide.

Figure 8:
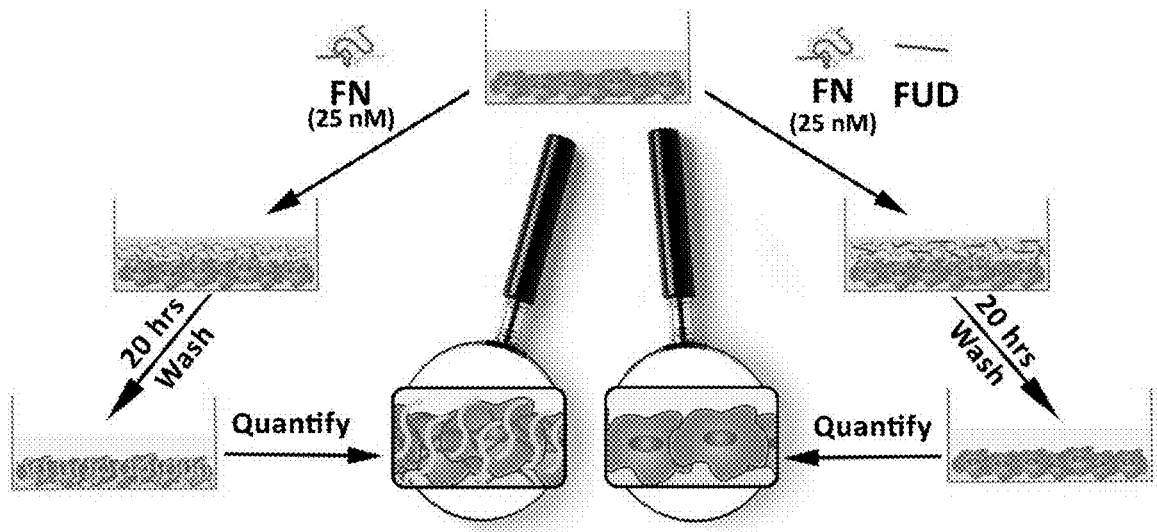
FIG. 8 shows a schematic representation of Matrix Assembly in vitro Assay (MAA) methodology. Human foreskin fibroblasts (AH1F) were grown in the presence of exogenous Alexa 488-labeled human plasma FN and in the presence or absence of an inhibitor.
Figure 9:
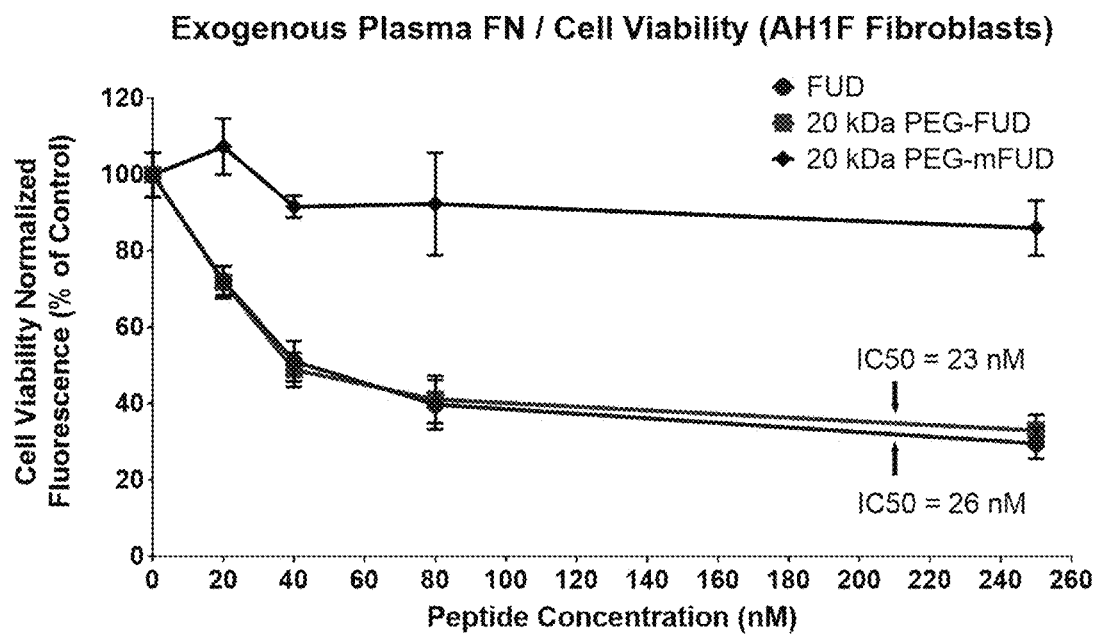
FIG. 9 shows a Matrix Assembly in vitro Assay (MAA) demonstrating inhibitory potency parity of FUD and 20 kDa PEG-FUD conjugates, and lack of inhibitory efficacy of the 20 kDa PEG-mFUD control peptide. Extraction of IC50 values yielded 26 nM and 23 nM for FUD and 20 kDa PEG-FUD, respectively. For each data point, n=4.
Figure 10:
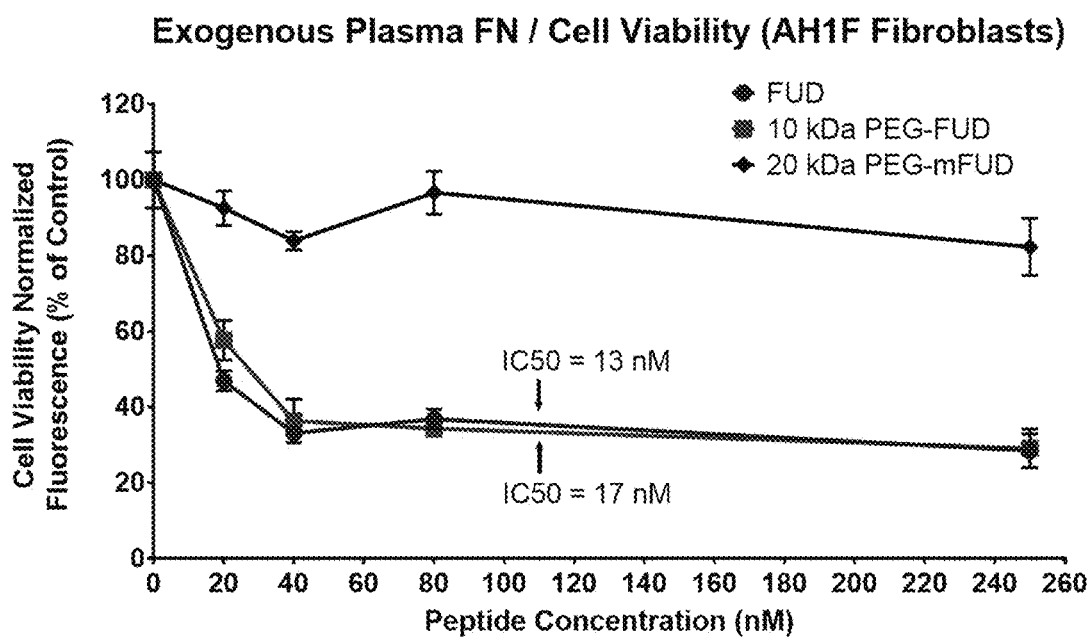
FIG. 10 shows a Matrix Assembly in vitro Assay (MAA) demonstrating inhibitory potency of FUD and 10 kDa PEG- FUD, and lack of inhibition with the 20 kDa PEG-mFUD control peptide. Extraction of IC50 values yielded 13 nM and 17 nM for FUD and 10 kDa PEG-FUD, respectively. For each data point, n=4.
Figure 11:
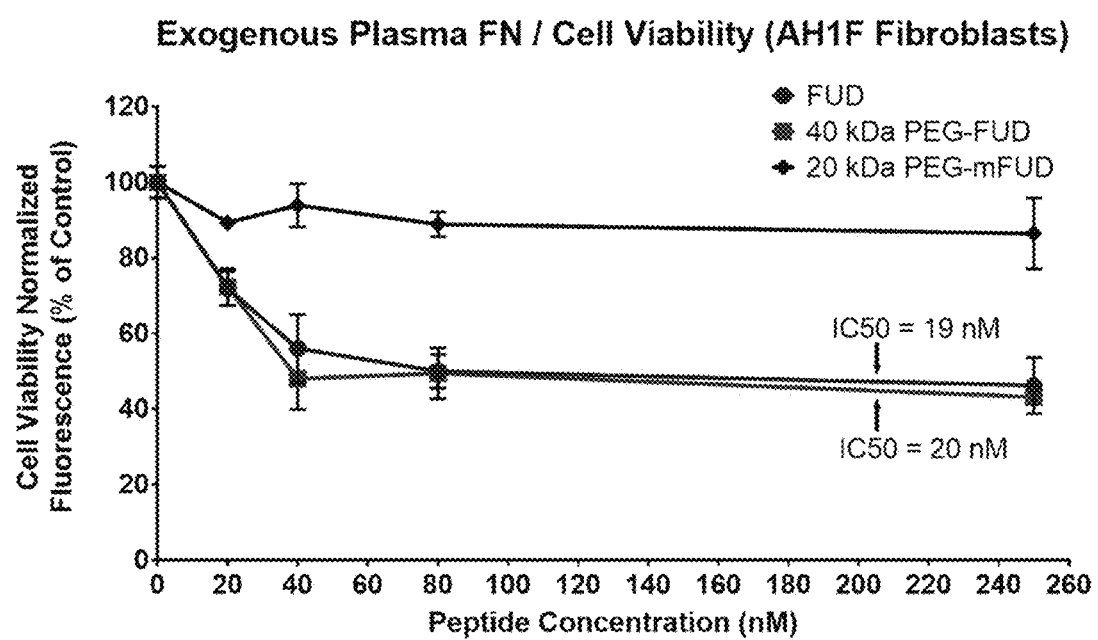
FIG. 11 shows a Matrix Assembly in vitro Assay (MAA) demonstrating inhibitory potency of FUD and 40 kDa PEG-FUD, and lack of inhibition with the 20 kDa PEG-mFUD control peptide. Extraction of IC50 values yielded 19 nM and 20 nM for FUD and 40 kDa PEG-FUD, respectively. For each data point, n=4.

The PEG-FUD FN fibrillogenesis inhibitory performance was evaluated in vitro using the matrix assembly assay (MAA). The methodology of this assay is depicted in FIG. 8. The MAA quantifies ECM deposition of exogenous AlexaFluor® 488-labeled FN (A488FN) by a confluent monolayer of fibroblasts after an incubation period by measuring fluorescence of deposited FN. In this study, the performance of PEG-FUD peptides was compared to that of FUD and the PEG-mFUD control peptide using the AH1F human foreskin fibroblast cell line. As shown in FIG. 9, the normalized fluorescence intensity of the PEG-mFUD control peptide group was found to be maximal and with no statistically significant differences from the 0 nM control group. This concentration independence indicates that the PEG-mFUD peptide demonstrates no FN fibrillogenesis inhibition over the concentration range studied (0-250 nM). The cell viability normalized fluorescence intensity of FUD, 10 kDa PEG-FUD, 20 kDa PEG-FUD, and 40 kDa PEG-FUD experimental groups rapidly declined with increasing peptide concentration. The calculation of IC50 values produced an IC50 of 17 nM for 10 kDa PEG-FUD vs 13 nM of FUD, 23 nM for 20 kDa PEG-FUD vs 26 nM of FUD (FIG. 9), and 20 nM for 40 kDa PEG-FUD vs 19 nM of FUD. Results of 10 kDa and 40 kDa MAA experiments are available in FIG. 10 and FIG. 11. As ascertained by student's t test, the means of cell viability normalized fluorescence intensity values at each drug concentration for the three PEGylated peptides were not significantly different from those of FUD. The PEGylated FUD conjugates thus showed a parity of inhibitory performance compared to FUD. This experiment demonstrates that despite PEGylation, the 10 kDa, 20 kDa and 40 kDa PEG-FUD constructs retain FUD's strong ability to inhibit FN fibril assembly. These MAA findings complement ITC experiments verifying a parity of binding affinity. Together, the ITC and MAA data both demonstrate that the PEGylated FUD constructs are equally potent FN fibrillogenesis inhibitors and that PEGylated mFUD is a valid control peptide.

TABLE I

ITC Binding Parameters

| Interaction | [FN] µM | [Peptide] µM | T ° C. | n | Kd nM | ΔG kcal mol$^{-1}$ | ΔH kcal mol$^{-1}$ | ΔS cal mol$^{-1}$ |
|---|---|---|---|---|---|---|---|---|
| FUD:FN | 1.7-1.8 | 23-29 | 25 | 1.59 | 6 | −11.4 | −31 | −65 |
| stdev | | | | 0.06 | 3 | 0.3 | 1 | 3 |
| 10K PEG-FUD:FN | 2.0-2.4 | 37-38 | 25 | 1.55 | 4.6 | −11.39 | −34 | −74 |
| stdev | | | | 0.06 | 0.5 | 0.09 | 2 | 7 |
| 20K PEG-FUD:FN | 1.0-2.7 | 25-42 | 25 | 1.63 | 10 | −10 | −30 | −66 |
| stdev | | | | 0.07 | 2 | 1 | 1 | 7 |
| 40K PEG-FUD-FN | 1.8-2.0 | 28.8 | 25 | 1.43 | 14.7 | −10.91 | −32.5 | −73 |
| stdev | | | | 0.05 | 0.9 | 0.02 | 0.5 | 2 |

Discussion of Examples 1-3

Size-dependent reduction in renal clearance following PEGylation is one of the primary drivers of pharmacokinetic improvement that can be considered in designing an enhanced FUD peptide. PEG size selection provides for the reduction in filtration of the glomerulus of the kidney to be sufficiently significant. Studies tracking $^{125}$I-labeled PEG of different sizes after i.v. infusion point to urinary clearance of PEG abruptly decreasing around the molecular weight of 30 kDa. Another study reinforces these findings with an immunohistochemical approach. Upon i.v. infusion, PEG immunoreactivity in the proximal renal tubules was found to diminish accordingly with PEG sizes of 10 kDa, 20 kDa, and 40 kDa, reiterating the size dependence of glomerular penetration. These observations were used to select a PEG sizes of 10 kDa, 20 kDa, and 40 kDa for PEGylation of the FUD peptide. The design intended for the individual constructs to have a nominal molecular weight that is smaller (~16.9 kDa), intermediately sized (~27.4 kDa), and large (~49.6 kDa). This diversity of molecular weights provides therapeutic candidates with increasingly reduced renal filtration behavior, expecting for the larger 40 kDa PEG-FUD to gain greatest plasma residence time improvements. The size of the PEG-FUD constructs was thus chosen strategically.

While the method of PEG conjugation was chosen with the intent of minimizing PEGylation-related binding affinity reduction, it was unexpected for a parity of inhibitory potency to be observed between FUD and PEG-FUD peptides. There exist numerous examples of PEGylation diminishing its target's activity. This reduction can vary from notable (PEG-IFN-α2b: 3.6 fold, $PEG_2$-IFN: 14 fold, PEG-B2036: 28 fold), to reducing activity by several orders of magnitude (PEG-G120K-GH: 186 fold). Some causes of this effect include disruption of the target's secondary structure and thus its binding motif, and steric interference of the binding site via proximal conjugation. Because FUD assumes a beta strand conformation upon binding with FN, the nature of the ligand/target interaction opens the possibility of secondary structure interference by a PEG spectator. This possibility contributed to uncertainty in predicting the binding affinity of PEG-FUD. Research suggests that FUD binding to FN involves many residues that are located along an extensive part of the peptide that together contribute to the peptide's tight nanomolar avidity for the 70K region of FN. It was intended for N-terminal PEGylation to be far removed from the core of this interaction, thus reducing the possibility of steric interference and leaving more C-terminal residues unrestricted to bind FN. It was suspected, however, that some binding affinity reduction was unavoidable because previous research suggested that the N-terminus of FUD may be involved in the peptide's interaction with FN. Furthermore, when bound to FN, the N-terminus tail of FUD is positioned facing the central portion of FN. Thus, a large PEG moiety conjugated at the N-terminus of FUD is liable to interfere with the dynamic folding and interactions of FN domains, potentially disturbing the binding of FUD to FN. These two concerns thus illustrate the finding presented herein are surprising. The retained low nanomolar binding affinity and unaffected FN fibrillogenesis inhibitory potency of PEG-FUD is unexpected and presents a unique property of the FUD peptide that can be exploited in applications using FN as a therapeutic target but for which the nature of peptide pharmacokinetics reduces FUD usefulness as a therapeutic candidate.

Organ fibrosis and fibrosis-associated progression of cancer are two application spaces in which a PEGylated fibronectin inhibitor may hold added therapeutic potential. The success of FUD fibronectin inhibition therapy in a mouse model of liver fibrosis suggests that this approach may be applied to other models of fibrosis that involve less accessible organs than the liver if the drug's pharmacokinetic properties are appropriately adjusted. Administration of a PEGylated FUD variant has the potential of improving FUD penetration into the kidneys by increasing the drug's circulation time, thus pointing to PEG-FUD as a potential therapeutic for the treatment of renal fibrosis. Recently published work suggesting that structural alterations of peritubular capillaries associated with renal fibrosis allow increased extravasation of solutes as large as albumin (65-70 kDa) and fibrinogen (340 kDa) into the peritubular interstitium also present a tantalizing possibility for improved delivery of a long circulating therapeutic with an enhanced molecular weight. Previous successes, combined with this observation, stress the importance of PEG-FUD therapeutic efficacy evaluation in the renal fibrosis context.

Fibrosis-associated progression of cancer also presents an area of research for which PEG-FUD could be a strong therapeutic candidate. Fibronectin and collagens have been implicated in the growth, migration, and invasion ability of a variety of tumors. Research has shown that fibrotic tissue is associated with a predisposition for development of both lung cancer and breast cancer. This concept is especially relevant to cancer cell shedding and development of metastasis in fibronectin-rich tissue. For example, this "priming the soil" effect has been observed with ovarian cancer cells secreting TGFβ, thereby inducing secretion of fibronectin by mesothelial cells which in turn facilitate adhesion, proliferation, and metastasis of ovarian cancer. Other research has shown that colonization of circulating breast cancer 4T1 tumor cells is doubled in two models of lung fibrosis and increased by 50% in one model of liver fibrosis. These findings suggest value in evaluation of fibronectin inhibition as a strategy for metastasis mitigation. A PEGylated FUD peptide with equal potency but tailored pharmacokinetic profile may be a very useful tool in studying this therapeutic strategy against fibrotic cancers.

The FUD peptide was successfully conjugated with 10 kDa, 20 kDa, or 40 kDa PEG moieties and isolated in good purity. The mass of the PEG-FUD constructs agreed with attachment of a single PEG molecule. Unexpectedly, retention of low nanomolar binding affinity was found following PEGylation with all three constructs. Furthermore, all three PEG-FUD peptides were found to be equally effective at inhibiting FN fibrillogenesis in vitro compared to unmodified FUD. These results suggest anti-fibrotic value of this peptide and stress the importance of evaluation of these PEG-FUD constructs in the context of therapeutic efficacy and pharmacokinetic performance in an animal model of fibrosis.

Materials and Methods: PEG-FUD as an Inhibitor of Fibronectin Fibrillogenesis Inhibits Fibrosis in UUO Kidneys PEG-FUD was prepared as in Example 1.

Microtiter fibronectin matrix assembly assays: Exogenous plasma fibronectin matrix assembly assay: Binding and incorporation of AlexaFluor® 488-plasma fibronectin (A488-FN) to fibroblast monolayers (human foreskin fibroblasts, AH1F cells was carried out using methods known in the art. Briefly, fibroblasts (60000 per well) were allowed to adhere and spread for 2 hours in microtiter plates in 2% fetal calf serum (FCS)-containing DMEM. Peptides or modulators to be tested were added followed by 28 nM A488-FN. Cell monolayers with or without peptides and A488FN were incubated overnight at 37° C. with 5% $CO_2$. Cell monolayers in microwells were washed with PBS or HBSS containing $Ca^{2+}$, $Mg^{2+}$. Fluorescence in 96-well plates was read using a microplate reader using bottom-readout capabilities at 485 nm excitation and 525 nm emission with 20 nm bandwidths. To estimate cell viability per well after the washes and measurement of fluorescence, an equal volume of luminescence reagent (Cell Titer-Glo®) was added followed by quantification of luminescence. Fluorescence of wells to which A488FN had not been added, i.e. intrinsic fluorescence of the cell monolayer was subtracted from fluorescence values of wells containing ligand. Data is presented respectively for fibronectin fibrillogenesis or cell viability as percent of fluorescence or luminescence values for wells with no peptides. Microplate microscopy was used to ascertain that fluorescence measurements correspond to fibrillary fibronectin.

Endogenous (cellular) fibronectin assembly assay: This immunochemical assay measures the ECM incorporation of EDA-containing fibronectin synthesized by human fibroblasts and human proximal tubular epithelial cells. Human proximal epithelial cells, HK-2 cells, were obtained from ATCC (CRL-2190). The EDA+ fibronectin is a splice variant synthesized and secreted by a variety of cells mostly during embryonic development and during wound healing, ECM remodeling, or fibrotic conditions in the adult. Fibroblasts (AH1F) were cultured in DMEM (Gibco) containing 10% fetal calf serum, and human proximal tubular epithelial cells (HK-2) were cultured in keratinocyte serum free medium (KSFM, containing pituitary extract and rEGF, Invitrogen/Thermo Fisher). Both media also contained 2.5 mM glutamine, 100 IU/ml penicillin, and 100 µg/ml streptomycin. Confluent cells were trypsinized and resuspended in DMEM containing 2% FCS in DMEM for AH1F cells or KSFM for HK-2 cells, at densities that allow delivery of 60,000 AH1F or 20,000 HK-2 cells in 90 µl per well in black-walled, flat transparent bottom 96-well plates. Cells were incubated for 2 h at 37° C. with 5% $CO_2$ and checked microscopically for spreading and confluence. Peptides were then added in 10 µl volumes at 10-fold the desired final concentration. Cell monolayers in microplates were incubated overnight in a humidified 37° C., 5% $CO_2$ chamber. After approximately 22 h, 10 µl of AlamarBlue® was added to the cell monolayers and incubated at 37° C. for 2 h to assess cell viability. Fluorescence of AlamarBlue® was read at 555 nm excitation and 585 nm emission. Microplates were washed twice with HBSS containing $Ca^{2+}$, $Mg^{2+}$ and 50 µl/well of 4% paraformaldehyde (PFA) in PBS was then added for 10 min at room temperature. Following two PBS washes, 100 µl 2% BSA/PBS was added for 1 h at room temperature to block nonspecific binding. The BSA solution was removed and Alexa488-labeled anti cellular FN monoclonal antibody (A488-EDA, eBioscience/Thermo Fisher cat. No. 53-9869-82) or a control antibody, AlexaFluor® 488-labeled IgG1, diluted in 2% BSA/PBS to 2.5 µg/ml was added and incubated for 1 h at room temperature. Similar to the measurement of exogenous A488-FN fluorescence, A488-EDA fluorescence was read using microplate reader equipped with bottom-readout capabilities at 485 nm excitation and 525 nm emission. Fluorescence of wells to which A488-IgG was added, i.e., background green fluorescence from non-specific IgG binding and from the cell monolayer was subtracted from fluorescence values of wells incubated with A488-EDA. Data is presented for fibronectin fibrillogenesis or cell viability as percent of fluorescence values (AlexaFluor® 488 fluorescence or AlamarBlue®, respectively) for wells with no peptides.

Unilateral Ureteral Obstruction model. Male C57BL/6 mice were purchased from Envigo (Madison, Wis.) and housed in the Wisconsin Institutes for Medical Research animal facilities at the University of Wisconsin-Madison with ad-libitum access to food and water. Animals were maintained in humidity and temperature-controlled rooms under 12 h light/dark cycles. All work was conducted under protocol M5421, reviewed and approved by the University of Wisconsin-Madison Institutional Animal Care and Use Committee. All efforts were made to minimize suffering. The Unilateral Ureteral Obstruction (UUO) model is a rodent surgical model representing a human equivalent of acute kidney injury. Obstruction results in marked dilatation of the ureter together with reduced renal blood flow and glomerular filtration. Renal histology demonstrates tubular atrophy and increasingly severe interstitial renal inflammation and fibrosis. UUO or sham surgeries were performed as previously described on 10-week male C57BL/6 mice weighing approximately 20-23 g following acclimation to the vivarium facilities. Briefly, under 2% isoflurane anesthesia, the left kidney and ureter were exposed through a midline or a flank incision. The ureter was ligated using black braided 7-O silk suture material. The ligated ureter and kidney were returned to the abdominal cavity and the incision was closed in two layers with interrupted sutures and Vetbond™ tissue adhesive or staples. The right or contralateral kidney was used as a control. Sham operated animals were treated as the UUO animals except their ureter was not ligated. Animals were given ketoprofen (5 mg/kg) prior to returning them to their cages where they were kept on standard water and chow until sacrifice at the designated times. Peptides, PEGylated peptides or PEG were diluted in physiological saline, prepared for in vivo administration as described in the art, and administered subcutaneously at 0.3 mg per day (approximately 12.5 mg/kg). PEGylated peptide equivalent amounts were based on peptide concentration. Treatment injections were started three days following surgery and continued daily until 24 h before harvest at day 10. At harvest, under isoflurane, blood was collected from the aorta and both UUO and contralateral kidneys removed. Each kidney was sectioned and one half placed in 10% formalin for 24 h, stored in 70% ethanol until processing for embedding in paraffin, sectioning and histological staining. The other half of each kidney was trimmed to remove the medulla and frozen in liquid nitrogen until extraction for Western blotting.

Sham surgeries in which the left ureter was handled but not tied resulted in levels of fibronectin or collagen comparable to contralateral kidneys. Thus, the right, contralateral, kidney of each mouse was utilized as a control to the left UUO-treated kidney. The data from two cohorts of UUO-treated mice were combined for this study composed of the following groups (n): saline (n=5), PEG (n=4), FUD (n=5), PEG-FUD (n=8) and PEG-mFUD (n=3).

Histology and immunostaining: Paraffin-embedded tissues were sectioned at 4 μm and stained with H&E and Picrosirius Red, and IHC for fibronectin and CD45 for leukocytes. Picrosirius red staining is specific for collagens I and III and is considered to be superior to trichrome staining for quantitation of collagens. Staining for fibronectin was carried out using a rabbit polyclonal antibody to mouse fibronectin (RamFN) which was described in the art. RamFN diluted at 1:5000 required prior proteinase K antigen retrieval and was developed with ImmPRESS Rabbit Ig HRP. Staining for leukocytes was carried out using the pan leukocyte antibody rat anti-mouse CD45 (Leukocyte Common antigen, Ly-5, BD Pharmingen, clone 30-F11) at 1:100 after citrate pH 6.0 antigen retrieval and developed with ImmPRESS rat Ig HRP. RamFN and CD45 staining was counter stained with hematoxylin to demarcate nuclei.

Stained tissue sections were imaged using the 20× objective on an upright brightfield Nikon Eclipse 600 microscope. This microscope was also equipped with polarizer capabilities utilized to assess the birefringence of the picrosirius red-stained collagen fibers. Quantitation of birefringence or DAB product following development of HRP stains was carried out using Image J (Sun Microsystems.Ink) from 6 images from each mouse section obtained at random within the central cortical area and excluding large blood vessels and the kidney capsule.

Tissue extraction and immunoblotting: Kidney tissues were fractionated as described in the art. Tissues were homogenized in RIPA buffer containing 1% deoxycholate (DOC) at 0.1 g tissue per ml buffer, spun at 4° C. and the resulting pellets were resuspended in buffer containing 4M urea, 4% SDS and 1 mM DTT. The DOC-soluble supernatant constitutes the cytosolic/membrane fraction (lysates). Resuspended pellets were vortexed and heated to 95° C. for 5 min. This latter pool constitutes the tissue fraction containing mostly ECM proteins with some nuclear components. The protein concentration in the ECM fraction was obtained using the DC Protein Assay kit (Bio-Rad) and albumin standards diluted in the corresponding buffer. ECM fractions (pellets) or 1% DOC-soluble fractions (lysates) were run on 4-15% or 4-20% gradient gels SDS-PAGE (Bio-Rad) at 10 μg/well, transferred to nitrocellulose and incubated with antibodies to fibronectin (RamFN) or to FUD followed by HRP-conjugated anti-rabbit (LifeTech/Thermo, Waltham, Mass., USA). Relative quantitation of specific blotted protein was performed by assessing band intensities using Image J and normalizing to bands obtained with rabbit anti-Histone 3 rabbit IgG (CellSignalTechnology, Danves, Mass., USA) or goat anti-GAPDH-HRP conjugated IgG (Genscript, Piscataway, N.J., USA), which were used as loading controls for ECM or lysate fractions, respectively. Alternatively, for comparison of protein levels in UUO vs contralateral tissues, we utilized Ponceau Red staining of blotted proteins prior to blocking. Images of all proteins per lane were captured, intensities measured by Image J, and utilized as loading control for normalization. SuperSignal® West Femto for Maximum Sensitivitiy (ThermoFisher) was used as substrate for HRP-conjugated secondary antibodies used in Western blotting.

Antibody to FUD—Rabbit polyclonal antibody to FUD was custom-generated by Biomatik. The antigen used for rabbit immunization consisted of synthetic preparation of the C-terminal half of FUD/pUR4 coupled to KLH via an additional cysteine residue at the N-terminus: C-DKKLP-NETGFSGNMVETEDTKA (SEQ ID NO: 2). A portion of the resulting antiserum against FUD was purified by affinity chromatography on the synthetic peptide antigen coupled to an affinity matrix by the manufacturer. The titer of the affinity purified IgG was 1:128000 by direct ELISA (Biomatik). We have assessed this affinity purified antibody by Western blotting and use it at 0.7 μg/ml to assess reactivity with purified PEG-FUD and to ascertain its presence in kidney tissue extracts.

Statistics:

Graphpad Prism software was used to determine significant differences among treatment groups analyzing with Student t-test (unpaired, parametric, 2-tailed, without correction). Probability (p)≤0.05 was considered significant.

Figure 12:
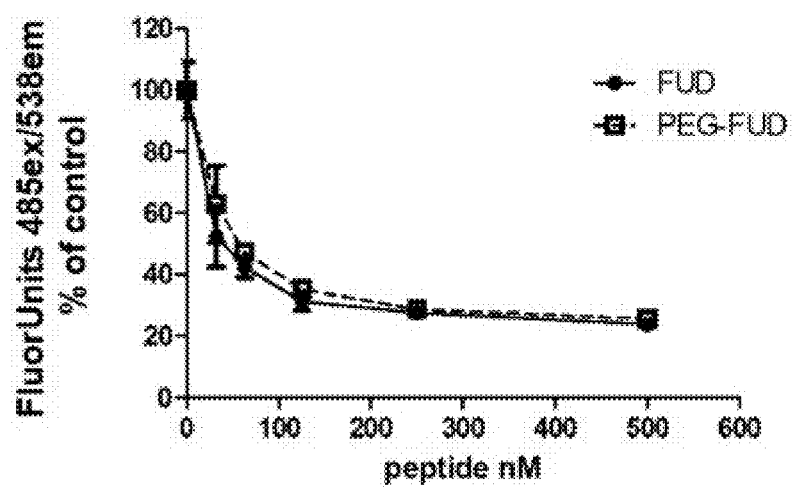
FIG. 12 shows microtiter assays measuring fluorescence associated with incorporation of fibronectin into ECM (left panel) and corresponding cell viability (right panel) following doses of FUD and PEG-FUD up to 500 nM, specifically human fibroblast incorporation of A488-plasma fibronectin. Data were collected in triplicate per dose and is depicted as mean+/−SD
Figure 12:
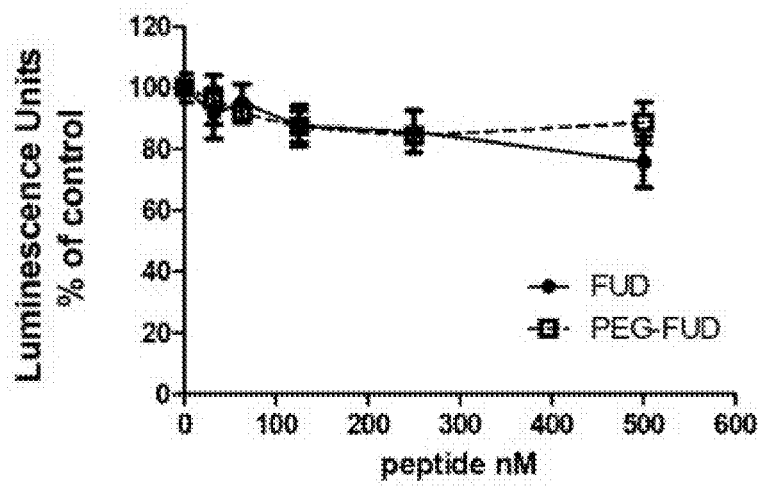
Figure 13:
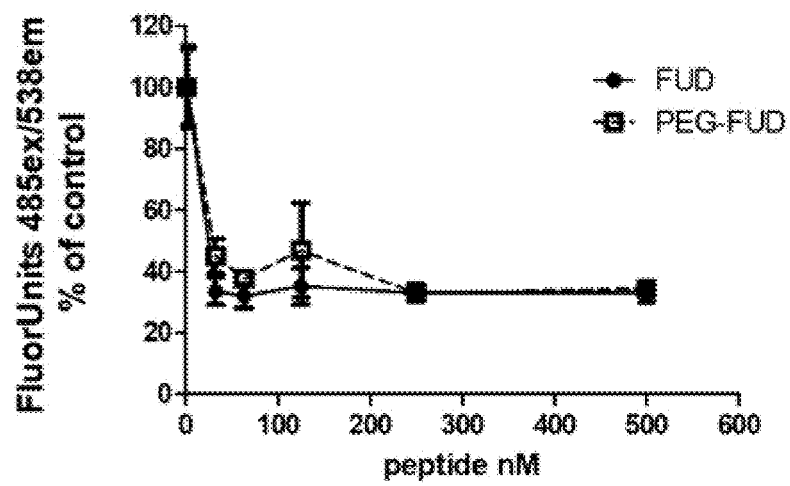
FIG. 13 shows microtiter assays measuring fluorescence associated with incorporation of fibronectin into ECM (left panel) and corresponding cell viability (right panel) following doses of FUD and PEG-FUD up to 500 nM, specifically for human fibroblasts. Data were collected in triplicate per dose and is depicted as mean+/−SD.
Figure 13:
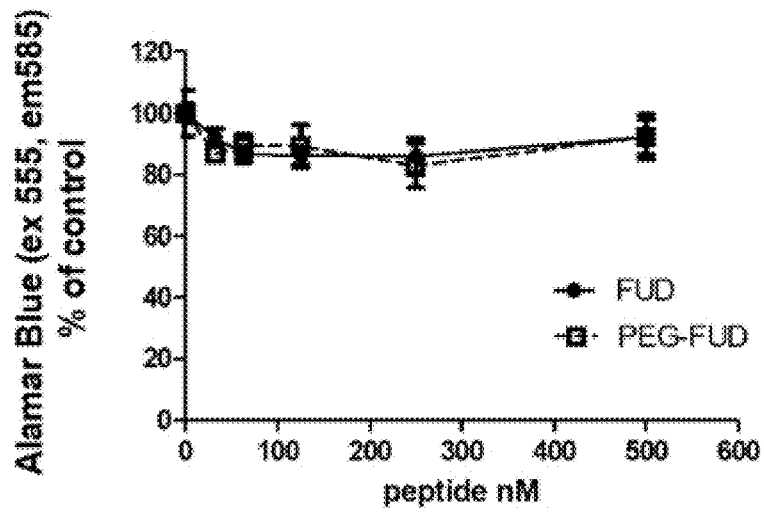
Figure 14:
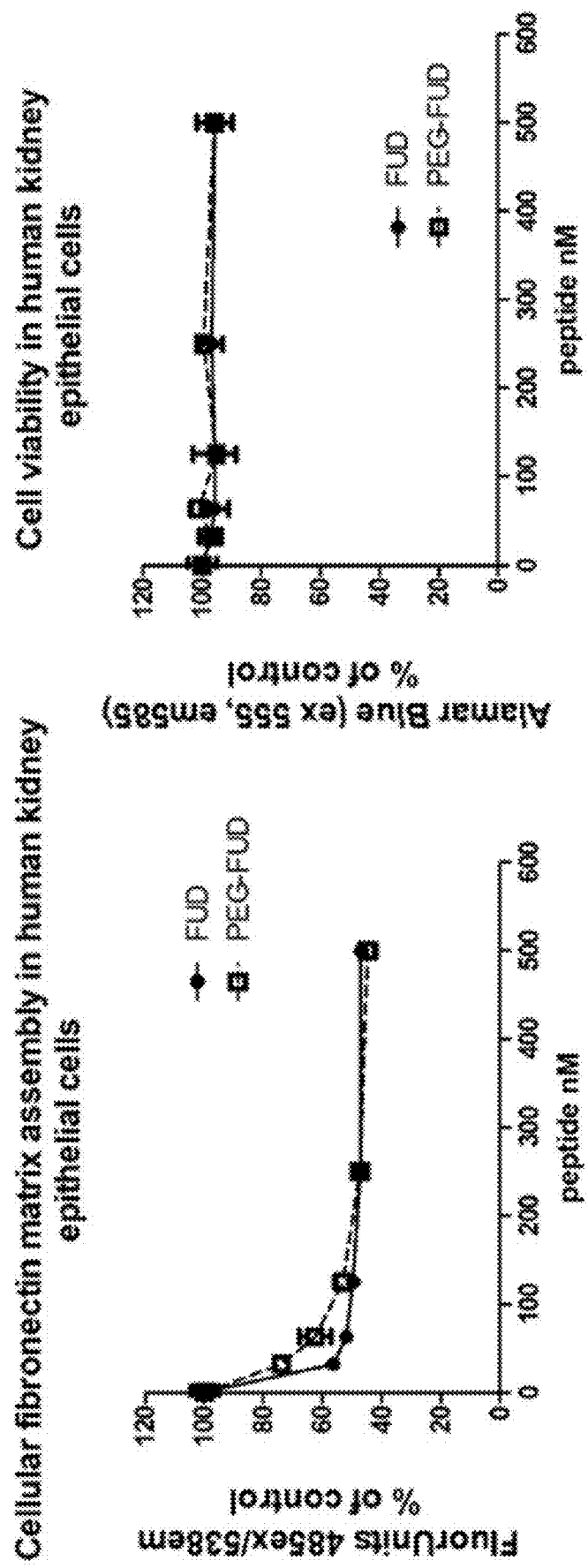
FIG. 14 shows microtiter assays measuring fluorescence associated with incorporation of fibronectin into ECM (left panel) and corresponding cell viability (right panel) following doses of FUD and PEG-FUD up to 500 nM, specifically human proximal tubular epithelial cell incorporation of cellular fibronectin recognized with A488-anti-EDA mAb. Data were collected in triplicate per dose and is depicted as mean+/−SD.

Example 4: Comparison of PEG-FUD with FUD as Inhibitors of Fibronectin Assembly In Vitro To determine whether PEG-FUD retained its ability to inhibit fibronectin fibrillogenesis, PEG-FUD and FUD were compared in cell-based fibronectin matrix assembly assays. The ability of PEG-FUD to inhibit the incorporation of exogenous fibronectin derived from plasma and also of fibronectin endogenously produced by the cultured cells was measured, since fibrosis is likely to contain fibronectin from both sources. Shown in FIG. 12 is the level of fibrils formed from exogenously added A488-FN fibrils in the presence of increasing amounts FUD or PEG-FUD. FIGS. 13 and 14 show endogenous EDA+-fibronectin fibrillogenesis in human fibroblast and human proximal tubular epithelial cells, respectively. In all fluorescence panels, it is evident that PEG-FUD is as efficient as FUD at inhibiting fibronectin assembly dose-dependently with an IC50 of approximately 30 nM. As previously reported, cell viability is negligibly affected by FUD, and PEG-FUD behaves almost identically. There was an approximately 20% decrease in fibroblast viability at the highest concentration of FUD tested (500 nM) with PEG-FUD retaining fibroblast viability almost at 100%. Both FUD and PEG-FUD were more potent inhibitors of assembly of plasma and cellular fibronectin by fibroblasts (70% inhibition) than by proximal tubular epithelial cells (50% inhibition). Human proximal tubular epithelial cell viability was retained at approximately 100% with treatment by both FUD and PEG-FUD. Thus, PEGylation of FUD resulted in a conjugate with fibronectin fibrillogenesis inhibitory capacity similar to that of unconjugated FUD, as demonstrated for both human fibroblasts and human proximal tubular epithelial cells.

Example 5: Testing PEG-mFUD as Control Peptide Conjugate at High Concentrations

Having established the suitability of PEG-FUD as inhibitor of FN fibrillogenesis, a mutated form of FUD, mFUD, was tested as a control peptide. mFUD was PEGylated as described above and the conjugate tested in the exogenous A488-FN binding assay as described for FIG. 1A. Shown in FIG. 15, concentrations of PEG-mFUD up to 20 µM did not affect fibronectin fibrillogenesis, whereas PEG-FUD and FUD behaved as expected, inhibiting fibrillogenesis by 60%, with similar IC50s in the 25-30 nM range. The right panel in FIG. 2 shows cell viability remained stable at 80% at doses of PEG-FUD and FUD ranging from 1 to 20 µM, while even at the highest concentration used, PEG-mFUD had no effect on cell viability. A maximum concentration of 20 µM was tested because it approximates the concentration used in vivo, both in this study and in the liver fibrosis study.

Example 6: Assessment of PEG-FUD in Kidney Tissue Extracts

Figure 16:
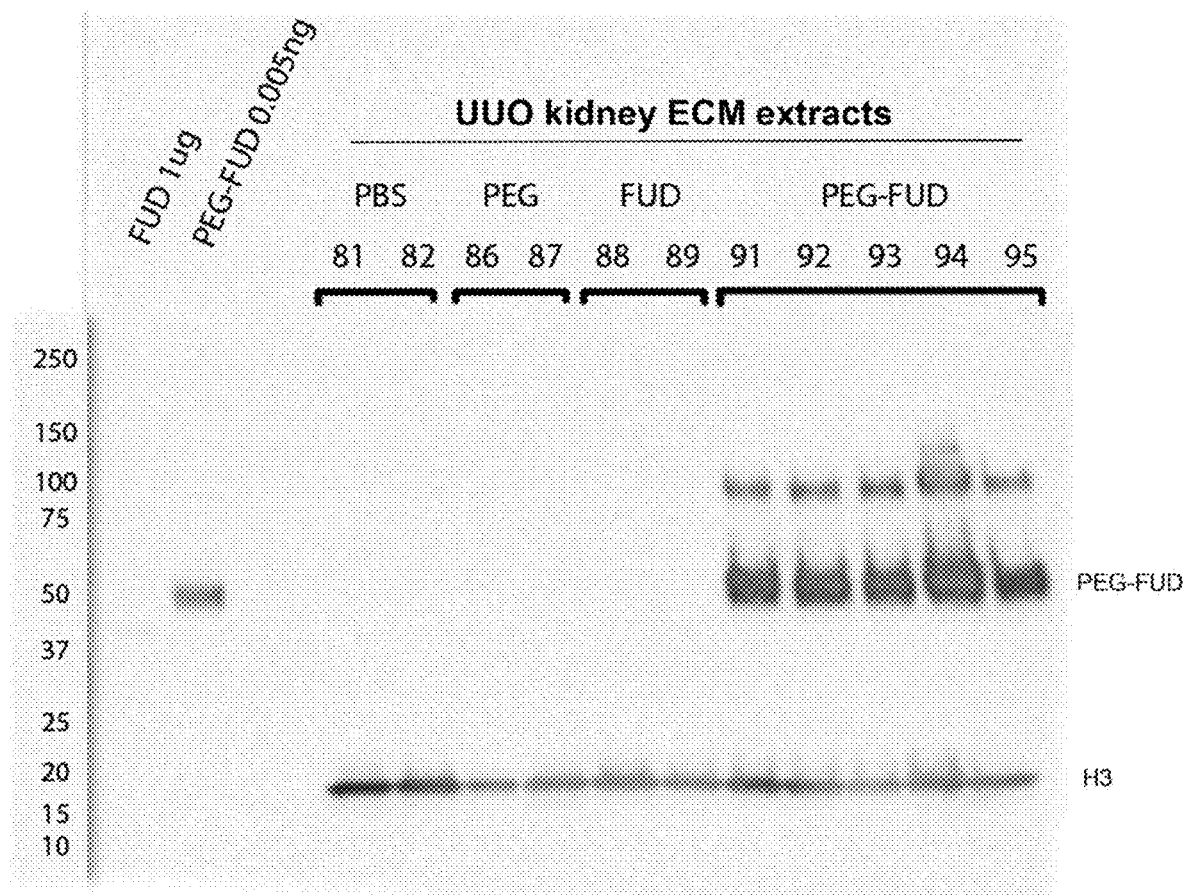
FIG. 16 shows immunoblotting of 10 µg/lane ECM fractions of UUO kidney extracts from mice subcutaneously administered with saline, PEG, FUD or PEG-FUD. The first two lanes contain purified FUD (1000 ng) and PEG-FUD (0.005 ng). Blot was reacted with 0.7 µg/ml rabbit polyclonal antibody generated to KLH-C-terminal half of FUD. Loading control for ECM fractions was achieved with rabbit-anti Histone3 (1:10000). Molecular weight markers are depicted to the left of the blot. Primary antibodies were followed by a 1:10000 dilution of anti-rabbit-HRP-IgG and chemiluminescence. Mouse ID numbers are depicted above corresponding lane. Note the polyclonal anti-FUD 1) recognizes PEGylated FUD much better than unconjugated FUD both in purified form and tissue extracts; and 2) is highly specific for the two bands associated with PEG-FUD without spurious reactivity towards other proteins in kidney tissues; 3) no PEG-FUD fragmentation was detected.

Because peptide therapeutics are often degraded in the circulation or filtered through the kidney before they have a chance to act, it was determined whether PEG-FUD reached the kidneys and if so, whether it remained intact. As shown in FIG. 16, PEG-FUD was identified in the ECM fractions of kidney extracts, recognized by an anti-FUD affinity-purified IgG. Note similar levels of intact PEG-FUD in kidneys of five different mice. Antibody recognition of PEG-FUD was specific with no spurious or background bands in the ECM fraction of kidney tissues from mice that were not administered PEG-FUD.

Figure 15:
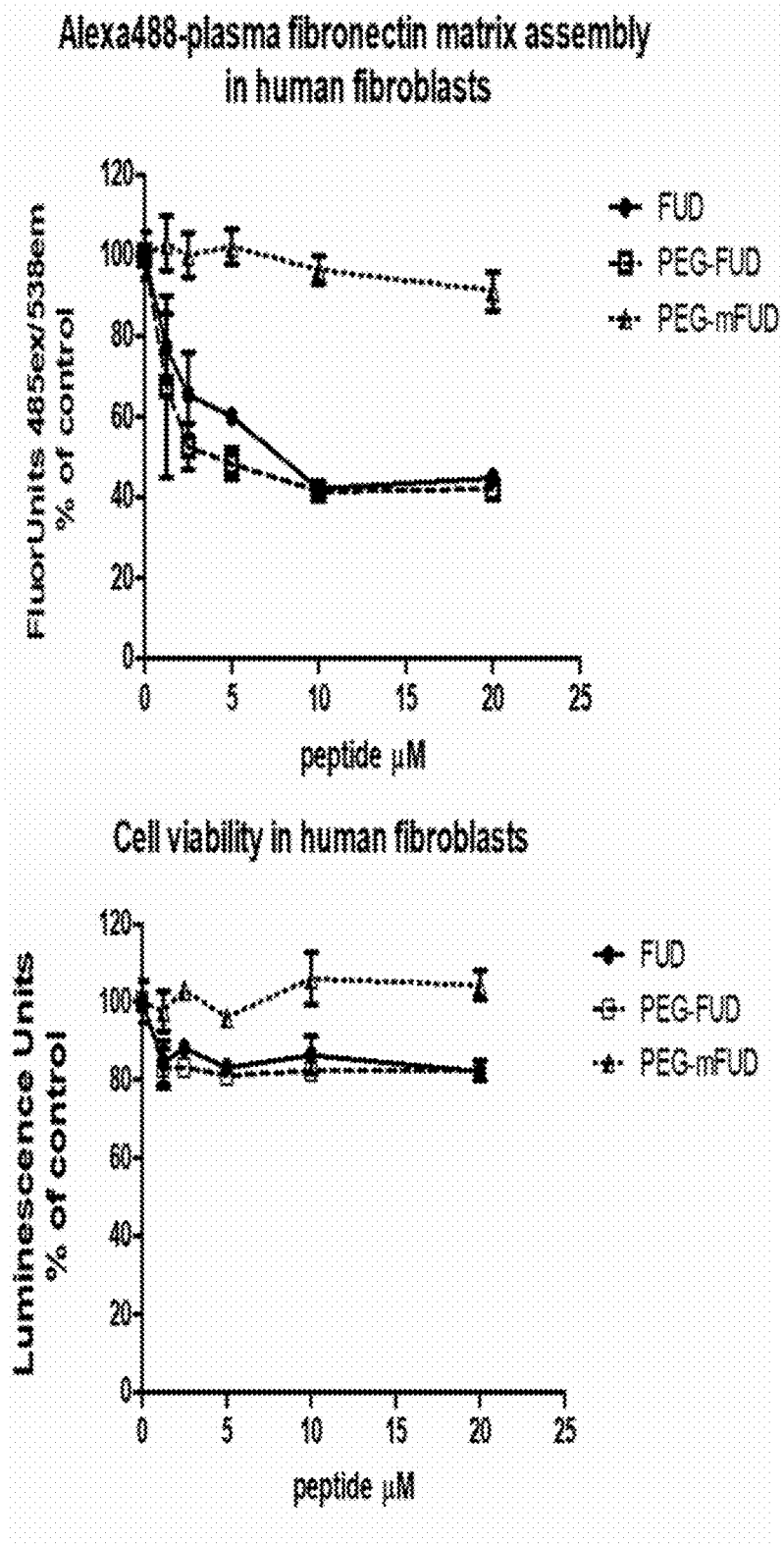
FIG. 15 shows a microtiter assay measuring fluorescence associated with A488-plasma fibronectin into ECM (left panel) and corresponding cell viability (right panel) following doses of FUD, PEG-FUD and PEG-mFUD up to 20 µM, approximating the dose used in vivo. Data was collected in triplicate per dose and is depicted as mean+/−SD.
Figure 17:
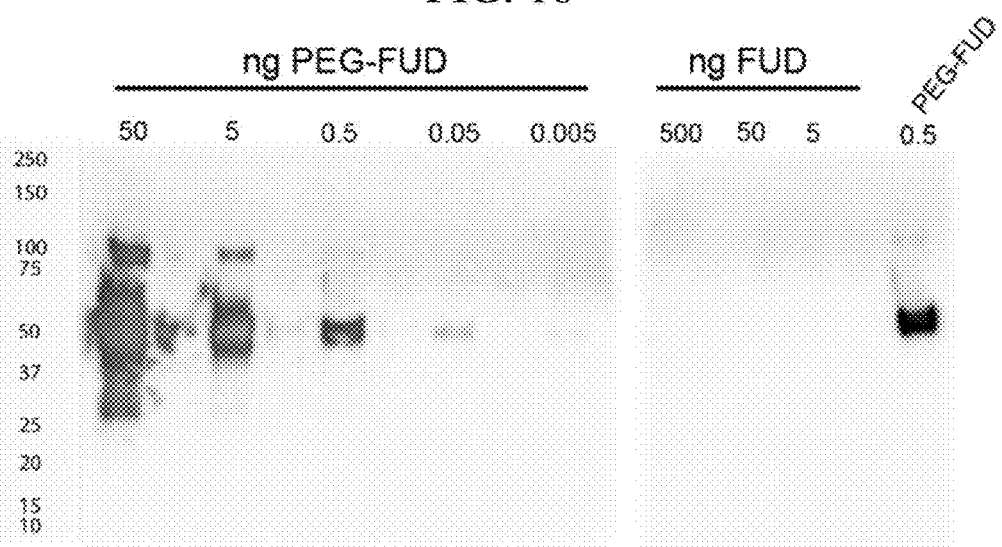
FIG. 17 shows purified PEG-FUD at 0.005, 0.05, 0.5, 5 and 50 ng per lane, and FUD at 5, 50 and 500 ng per lane were separated on a 4-20% gradient gel and immunoblotted with rabbit anti-FUD IgG at 0.7 µg/ml, followed by HRP-conjugated anti-rabbit IgG at 1:10000. Molecular weight markers are depicted to the left of the blot. PEG-FUD migrates primarily approximately at the 50 kDa mark with a less prominent band at 100 kDa. Recognition of PEG-FUD in the left blot was of high avidity with a sensitivity of 5 pg; band intensity correlated with amount of protein loaded per lane. The blot to the right shows recognition of unconjugated FUD was almost nil. PEG-FUD at 0.5 ng was also run in this blot as a positive control.
Figure 18:
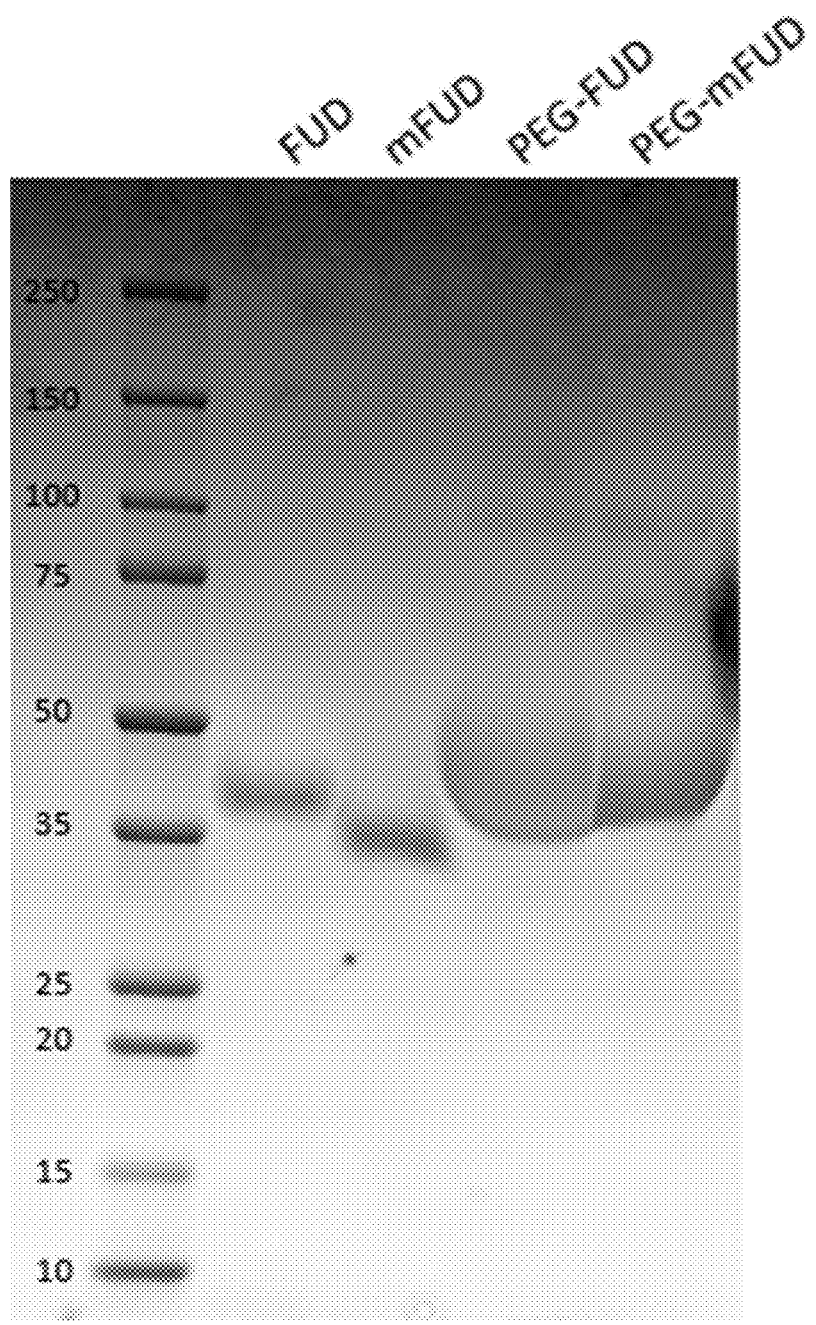
FIG. 18 shows purified FUD, mFUD, PEG-FUD and PEG-mFUD were loaded onto a 4-20% polyacrylamide gel at 5 µg/lane, run as per standard conditions and stained with Coomasie Brilliant Blue. Molecular weight standards are depicted to the left of the gel. The molecular weights of FUD and of PEG-FUD are approximately 7 and approximately 27 kDa, respectively as determined by mass spectrometry. However, on SDS-PAGE, both migrate close to the 50 kDa marker. It is well recognized that short peptides (<10 kDa), can migrate anomalously on SDS-PAGE, depending on their axial ratios or hydrophobic amino acid content. In addition, PEG moieties are polydisperse and may also alter the electrophoretic mobility of its peptide conjugates. In the PEGylated peptides, there is a fainter band at 100 kDa, which may represent dimerization of the conjugate. Dimerization may occur upon handling or freezing and thawing of the conjugated peptide, but upon purification there was no dimerization detected by HPLC or mass spectrometry.

Interestingly, the antibody did not react with FUD in tissues as avidly as with PEG-FUD, as shown in FIG. 16. Incubation with anti-histone3 antibodies demonstrates similar amounts of protein extracts of UUO kidneys from mice treated with FUD. Both FIGS. 16 and 17 demonstrate differential antibody reactivity towards purified FUD and PEG-FUD. This is not entirely surprising because the antibody was generated against KLH-conjugated FUD and affinity purified on a peptide-agarose column, thus reactivity was elicited and enriched for affinity towards a conjugated version of FUD. The affinity purified antibody recognized 500 pg PEG-FUD but only faintly recognized 500 ng of FUD (FIG. 17). Similarly, faint reactivity to 1 µg purified FUD is shown in FIG. 15. As shown in FIG. 18, analysis by SDS-PAGE of purified peptides, loaded at 5 µg/lane to allow detection with Coomasie Blue, demonstrated comparable protein levels for FUD and PEG-FUD. PEGylated peptides appear as diffuse bands due to polydispersity properties of the PEG moiety. This confirms that the anti-FUD antibodies recognize PEG-FUD better than FUD as an intrinsic property of the antibodies and not because of differences in protein concentration assessment or loading onto SDS-PAGE gels.

Figure 19:
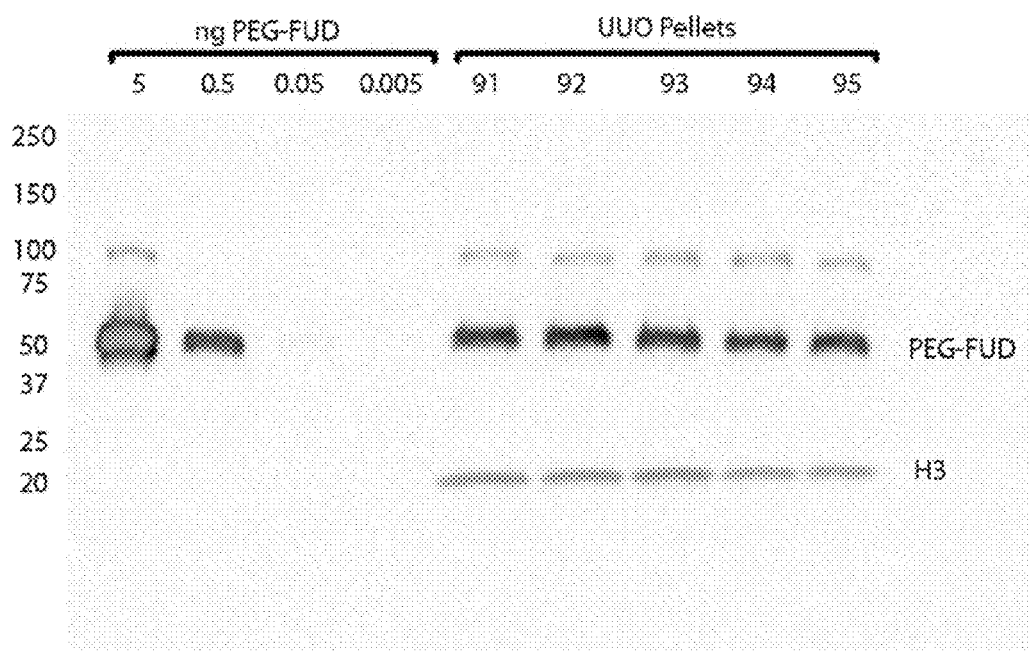
FIG. 19 shows an immunoblot of purified PEG-FUD at 0.005, 0.05, 0.5 and 5 ng compared to 10 µg pellet fractions of UUO kidneys from 5 mice administered PEG-FUD. Loading control was histone 3. Note consistency in levels of PEG-FUD in UUO ECM tissue fractions of 3 different mice. The intensity of the 50 kDa PEG-FUD band was deemed most similar to 0.5 ng of purified PEG-FUD. Thus, 0.5 ng/10 µg tissue protein was extrapolated to estimate 50 ng PEG-FUD per mg kidney tissue. Mouse ID numbers are depicted above corresponding lane. Molecular weight markers are depicted to the left of the blot.
Figure 20:
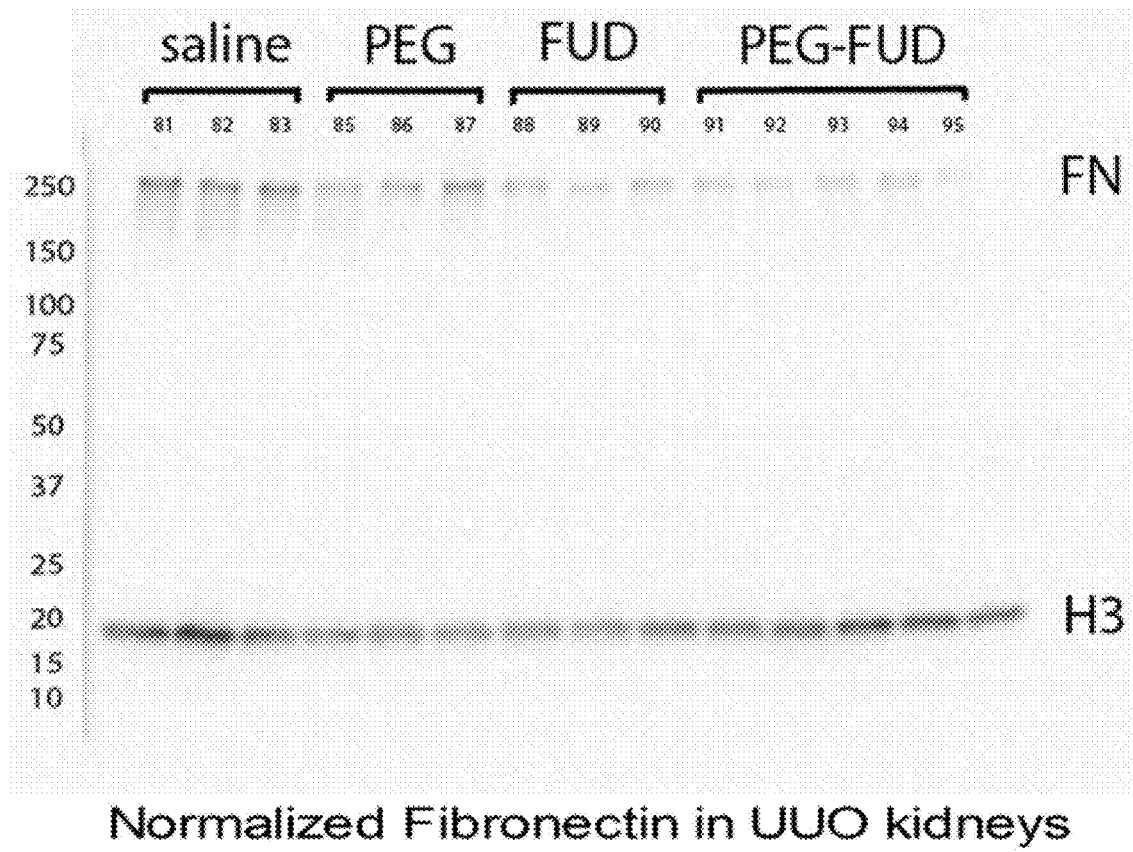
FIG. 20 is an immunoblot of ECM (pellets) and cytosolic/membrane (lysates) at 10 µg/lane from kidneys of mice treated with PEG-FUD. Purified PEG-FUD at 0.5 ng/lane was run for reference. Molecular weight markers are depicted to the left of the blot. Quantitation of the 50 kDa PEG-FUD band was carried out using Image J and normalized to protein bands visible in the central region of the blot with Ponceau stain. The means of the normalized intensities are presented+/−SD showing a slight enrichment of PEG-FUD in UUO kidneys compared to contralateral. Mouse ID numbers are depicted above corresponding lane Significance is denoted as * p<0.05.
Figure 21:
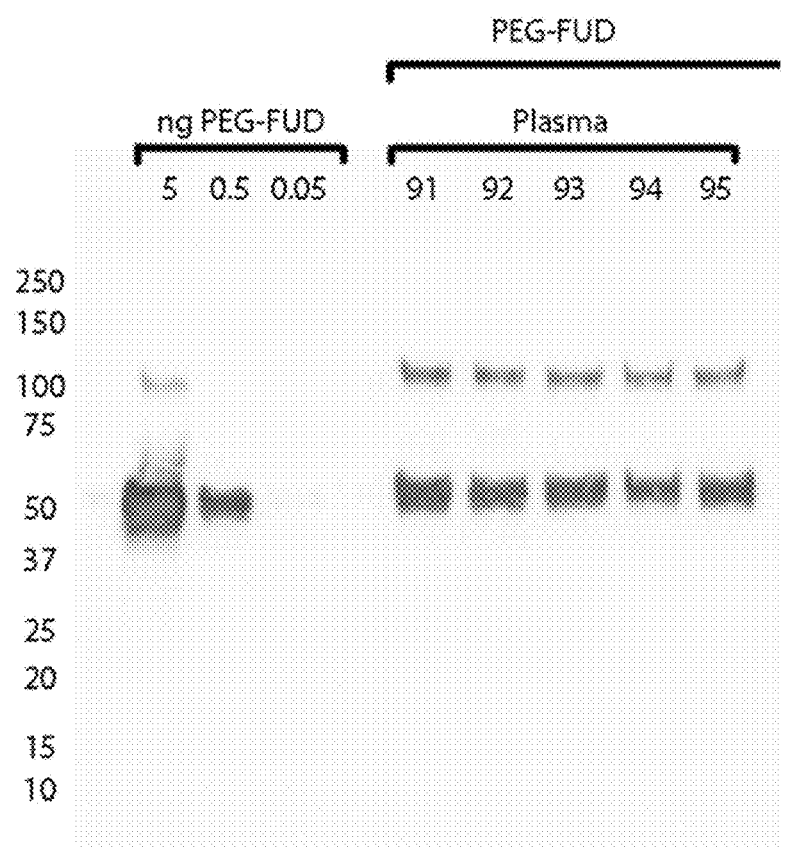
FIG. 21 shows an analysis of plasma collected at harvest from mice receiving PEG-FUD and diluted to 1:1000; 10 µl were loaded per lane. Purified PEG-FUD at 0.05, 0.5 and 5 ng/lane were added for reference. The blot was reacted with rabbit-anti-FUD IgG at 0.7 µg/ml followed by HRP-conjugated anti-rabbit IgG at 1:10000. As in tissues, the levels of PEG-FUD in plasmas from 5 different mice were also consistent. Circulating PEG-FUD appeared intact and was similar in intensity to the 0.5 ng PEG-FUD reference which suggests a circulating level of approximately 50 µg/ml (50 ng per 10 µl loaded×1000 dilution factor). Mouse ID numbers are depicted above corresponding lane. Molecular weight markers are depicted to the left of the blot.

FIG. 19 shows the sensitivity of the antibody for purified PEG-FUD under Western blotting conditions was as low as 5 pg, and the level of PEG-FUD present in 10 µg ECM fractions of UUO kidneys was comparable to 500 ng PEG-FUD. Extrapolation suggests levels approximating 50 ng PEG-FUD per mg of kidney protein. Note consistency of similar levels of PEG-FUD in kidney extracts of five different mice. FIG. 20 shows Western blotting for PEG-FUD in different kidney fractions. Distribution of PEG-FUD within the kidney suggested a tendency towards enrichment in UUO vs contralateral kidneys, but with similar levels in the ECM (pellets) compared to lysate fractions (FIG. 20). Normalization with loading controls for this blot was achieved with proteins stained with Ponceau Red to allow comparison of pellets vs lysates. PEG-FUD was present in both UUO and contralateral kidneys in intact form. Intact PEG-FUD was detected at consistent levels in plasma (diluted 1:1000) of 5 different mice. Extrapolating from varying amounts of purified PEG-FUD, the level of PEG-FUD in plasma may approximate 50 µg/ml (FIG. 21).

Example 7: Assessment of Fibronectin Deposition in Kidney ECM

Figure 22:
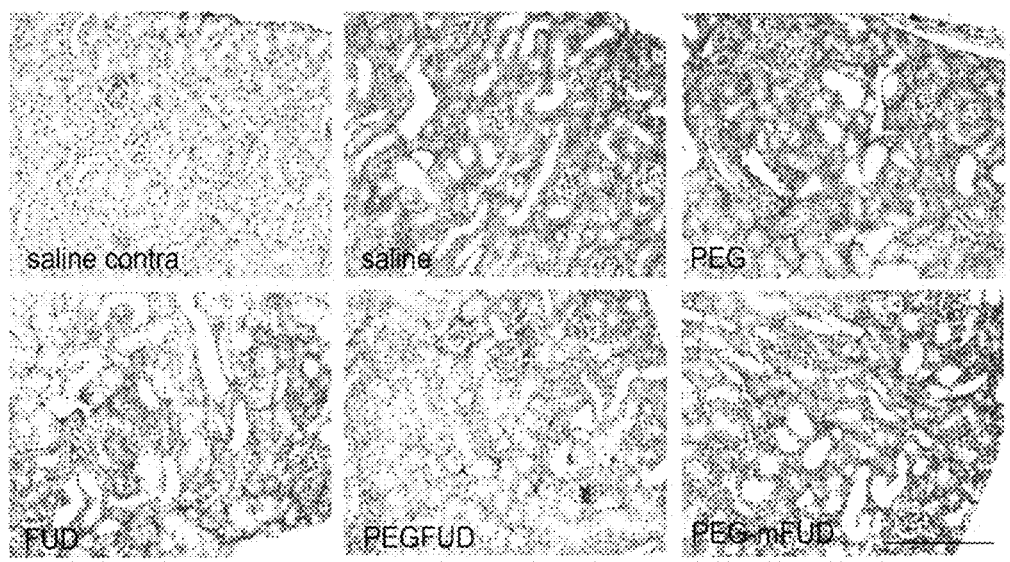
FIG. 22 shows representative images from the central cortex of 4 µm kidney sections stained with rabbit polyclonal antibody to fibronectin IgG (RamFN) at 0.5 µg/ml. UUO and contralateral kidneys were stained simultaneously. Except for the contralateral kidney of saline treated mice shown in top left panel, all other images are from UUO kidneys for comparison of treatment with saline, PEG, FUD, PEG-FUD and PEG-mFUD. Bar=200 µm. Quantitation of staining was performed using Image J and the mean of six images per treatment per cohort+/−SD is graphed. Significance is denoted as * p<0.001; p<0.01, *p<0.05.
Figure 22:
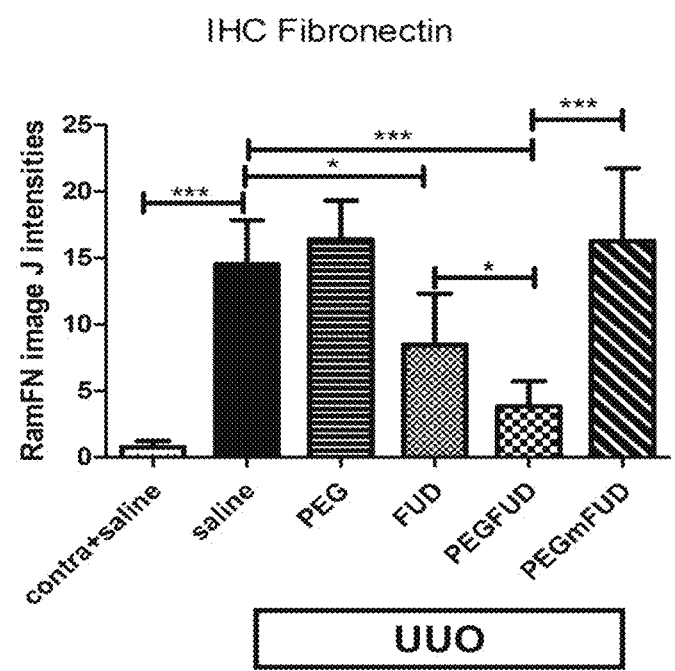

To determine whether FUD and PEG-FUD inhibited fibronectin deposition in kidneys of UUO-treated mice, fibronectin was assessed at the protein level, using immunohistochemistry and immunoblots of kidney extracts utilizing a previously described polyclonal antibody to mouse fibronectin. Shown in FIG. 22 are representative images from the cortical regions of kidneys from mice treated with saline, PEG, FUD, PEG-FUD or PEG-mFUD. As expected, fibronectin staining was detected in interstitial spaces and was greatly increased in the UUO kidney. The graph in FIG. 22 shows quantitation of this staining using Image J software and Student t-Test statistical comparison analysis. Fibronectin was significantly increased (approximately 14-fold) in UUO compared to contralateral kidneys. FUD and PEG-FUD significantly decreased fibronectin deposition by 40% and 70%, respectively. Neither PEG nor PEG-mFUD decreased fibronectin.

Figure 23:
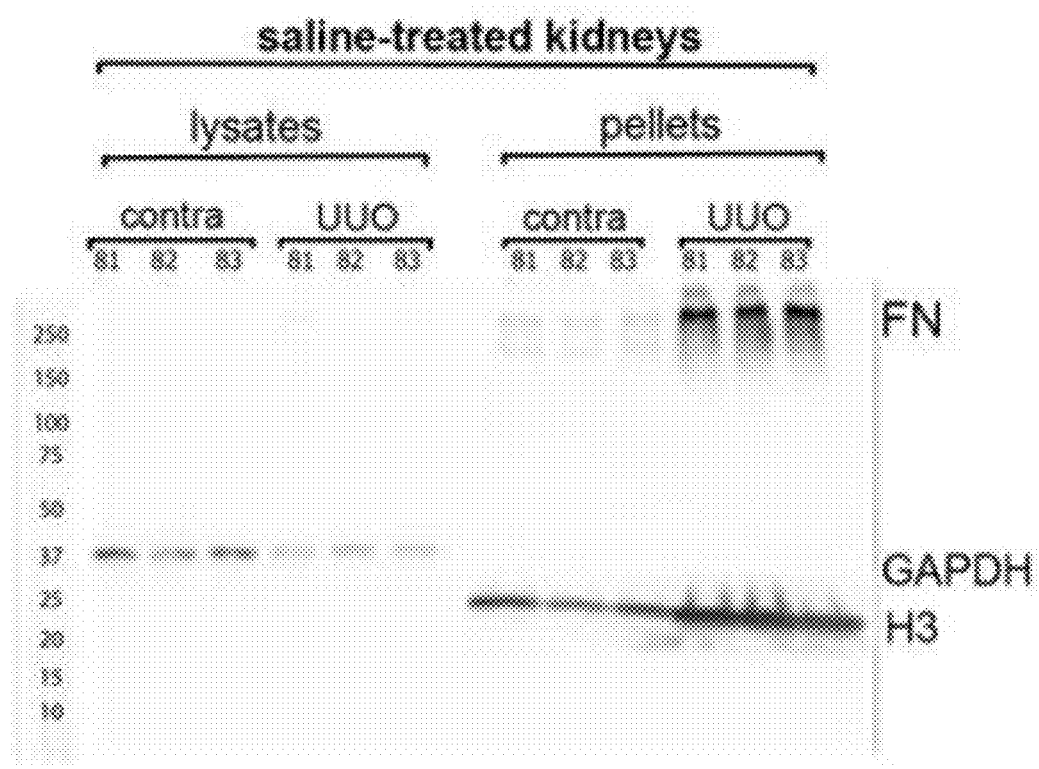
FIG. 23 shows the distribution of fibronectin into different tissue compartments analyzed by fractionation of UUO and contralateral kidneys from three different mice treated with saline (mouse IDs above lanes) into DOC-insoluble (pellets) corresponding largely to ECM and DOC-soluble (lysates) corresponding to cytosolic and membrane proteins (10 µg/lane). Western blotting was carried out incubating the blot with RamFN IgG at 2 ng/ml followed by anti-rabbit-HRP IgG at 1:10000. Loading controls were GAPDH for lysate fractions and histone 3 (H3) for DOC-insoluble fractions. Molecular weight markers are depicted to the left of the blot.
Figure 24:
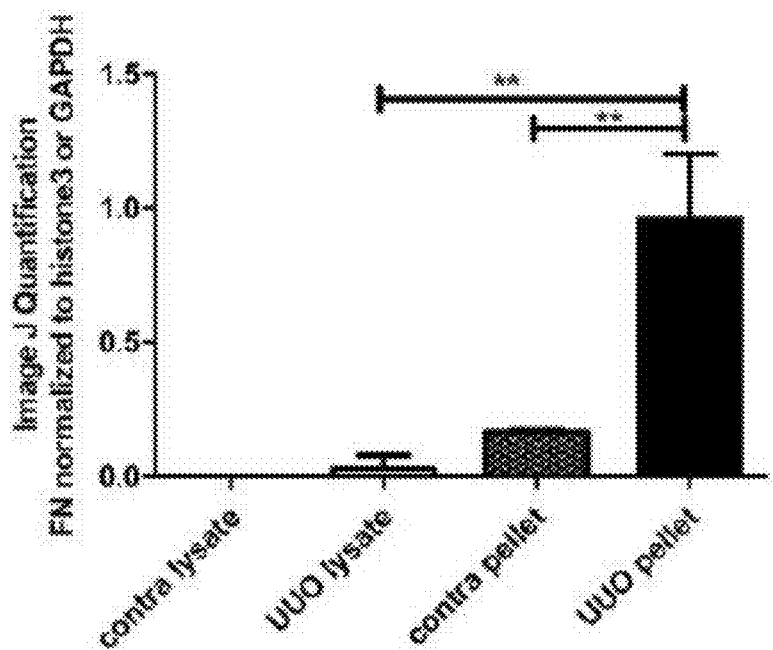
FIG. 24 shows quantitation of bands from FIG. 23 carried out using Image J. Mouse ID numbers are depicted above corresponding lane. The means of fibronectin (FN) bands normalized to loading control bands from three mice+/−SD are presented. Significance is denoted as ** $p<0.01$, as per Student t-Test analysis.

To corroborate this finding and determine whether the deposited fibronectin was intact or fragmented due to treatment, kidney tissues were extracted and separated into ECM and cytosolic/membrane fractions. It has been previously demonstrated in vitro that fibrillar fibronectin is typically enriched in the detergent-insoluble fraction (ECM fraction) of DOC extracted fibroblast monolayers, but to our knowledge, this has not been shown for kidney tissues. The cortical regions of kidneys were extracted with lysis buffer containing 1% DOC as described above. Following centrifugation, the soluble fraction was removed, termed "lysates" in this study, and the insoluble ECM fraction, termed "pellets" was solubilized with SDS-PAGE-loading buffer containing 4 M urea. FIGS. 23 and 24 show the distribution of fibronectin in extracts from three contralateral kidneys compared to the corresponding UUO extracts. As shown in FIG. 23, RamFN recognized the 250 kDa band expected for fibronectin in the pellets (ECM) from both UUO and contralateral kidney extracts under reducing conditions. Next to nil fibronectin was detected in the lysates (cytosolic/membrane) from either the UUO or contralateral kidney extracts. Surprisingly, no degradation of fibronectin was apparent in UUO tissues, despite the remodeling and proteolysis expected in tissue undergoing inflammation and oxidative stress. Histone3 and GAPDH were used as loading control molecules for normalizing fibronectin band intensities in pellets and lysates, respectively. Normalized values of fibronectin clearly indicated a significant enrichment of fibronectin in the ECM fraction of UUO compared to contralateral kidneys, as shown in FIG. 24.

Figure 25:
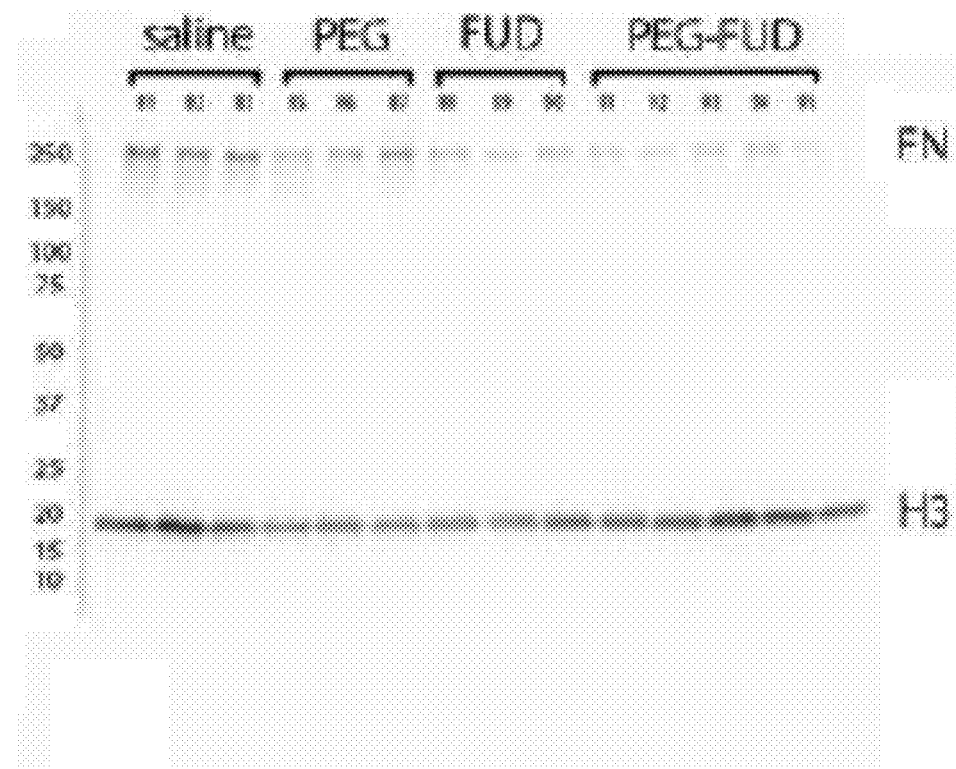
FIG. 25 shows and immunoblot of DOC-insoluble fractions from UUO kidneys (10 µg/lane) from mice treated with saline, PEG, FUD or PEG-FUD were immunoblotted using RamFN Ig. Mouse ID numbers are depicted above corresponding lane.
Figure 26:
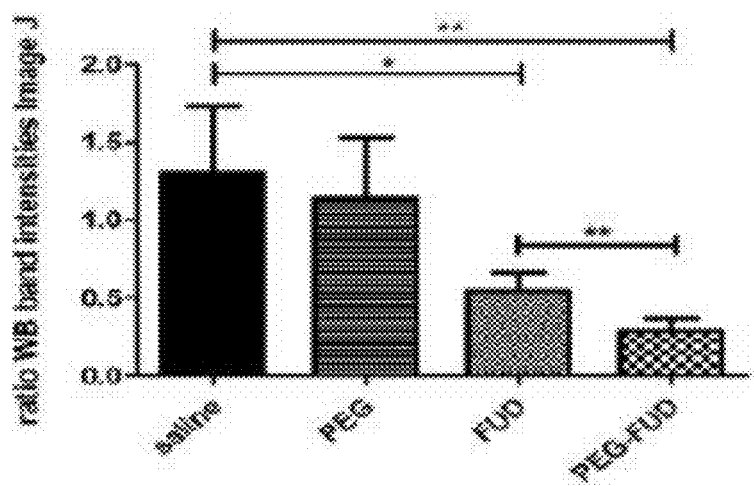
FIG. 26 shows quantitation of fibronectin and histone 3 band intensities from FIG. 25 carried out using Image J. The means of fibronectin (FN) bands normalized to H3 from 3 or 5 mice (as indicated)+/−SD are presented. Significance is denoted as * $p<0.05$; ** $p<0.01$, as per Student t-Test analysis.
Figure 27:
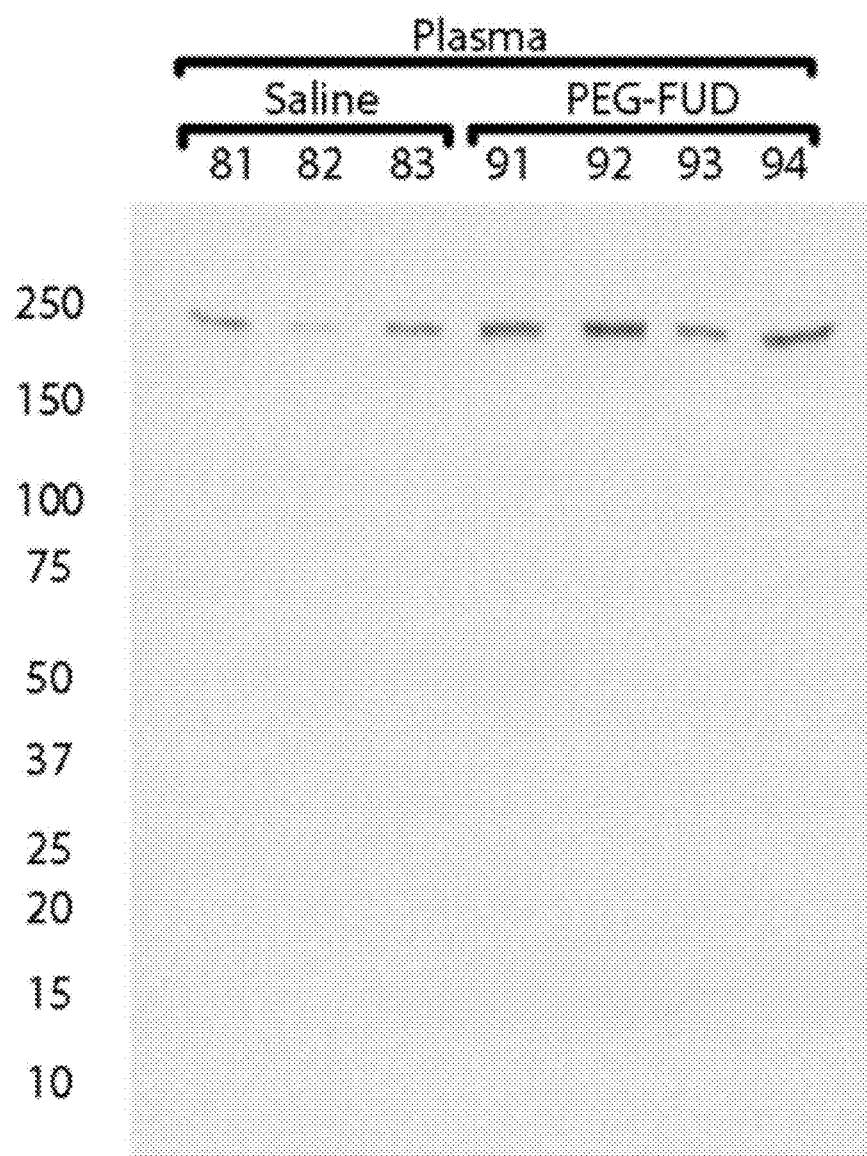
FIG. 27 shows plasma collected at harvest diluted 1:1000 and 10 µl loaded per lane. The blot was reacted with rabbit polyclonal to fibronectin (RamFN) at 2 ng/ml, followed by HRP-conjugated anti-rabbit IgG at 1:10000. Mouse ID numbers are depicted above corresponding lane. Molecular weight markers are depicted to the left of the blot.

Having shown that most FN is present in the ECM fraction of UUO kidneys, we focused on those fractions for further analyses. Shown in FIG. 25 is an immunoblot of ECM fractions from UUO kidneys of mice treated with saline, PEG, FUD or PEG-FUD reacted with anti-fibronectin antibody. Again, fibronectin was recognized as a 250 kDa band and histone3 at 17 kDa was utilized as a loading control. Relative quantitation of the intensities of fibronectin and histone3 bands using Image J is presented as normalized values shown in FIG. 26. Compared to saline-treated UUOs, FUD and PEG-FUD decreased fibronectin by approximately 60% and approximately 80%, respectively. PEG did not decrease fibronectin significantly. Again, no proteolytic fragments were detected with the polyclonal antibody to fibronectin, suggesting that inhibition of fibronectin deposition into kidney matrices does not render fibronectin susceptible to proteolysis. This was also the case for fibronectin in plasma (FIG. 27).

Example 8: Quantitative Assessment of Histological Collagen and Leukocytes

Figure 28:
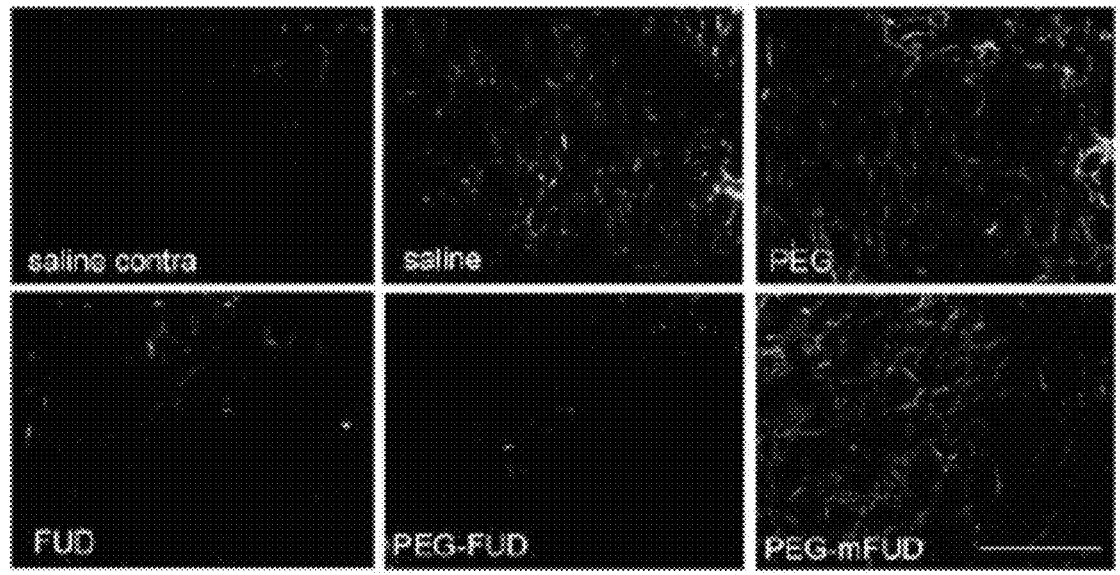
FIG. 28 shows representative images from the central cortex of 4 µm kidney sections stained with picrosirius red, which stains primarily collagens I and III. Birefringence elicited from exposure to polarized light was imaged. UUO and contralateral kidneys were stained simultaneously. Except for the contralateral kidney of saline treated mice, all other images are from UUO kidneys for comparison of treatment with saline, PEG, FUD, PEG-FUD and PEG-mFUD. Bar=200 µm. Quantitation of staining was performed using Image J and the mean of six images per treatment per cohort+/−SD was graphed. Significance is denoted as * $p<0.05$; ** $p<0.01$, as per Student t-Test analysis.
Figure 28:
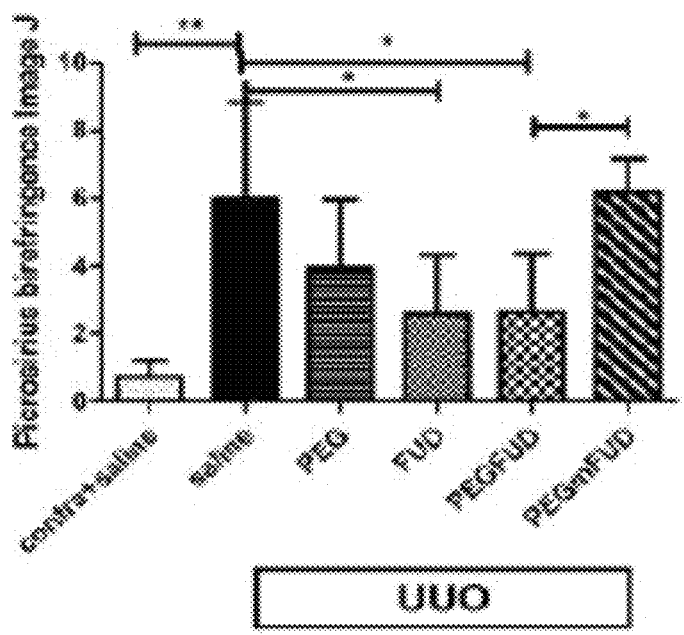

Once it was clear that PEG-FUD decreased fibronectin in the kidney, possible effects on collagen deposition and leukocyte infiltration were determined. Fibronectin has been shown to modulate and, in some microenvironments, control the deposition of collagens, structural proteins responsible for scar formation and increased tissue density associated with fibrosis. Collagens I and III were detected by illuminating picrosirius red-stained tissue sections with polarized light. The resulting birefringence associated with the collagen fibers was imaged and quantified using Image J. FIG. 28 shows representative images from kidney sections sequential to those described above for fibronectin. Contralateral kidneys of mice treated with saline show negligible collagen in the cortical interstitium (top, left panel). The corresponding UUO section (top central panel) shows increased collagen as expected for UUO-treated kidneys. Relative quantitation performed with Image J shows greater variability in collagen detection for most of the treatment groups than that observed for fibronectin. Nevertheless, there was a significant decrease in collagens in kidney sections of mice treated with FUD or PEG-FUD of about 50% and no significant effect with PEG or PEG-mFUD.

Figure 29:
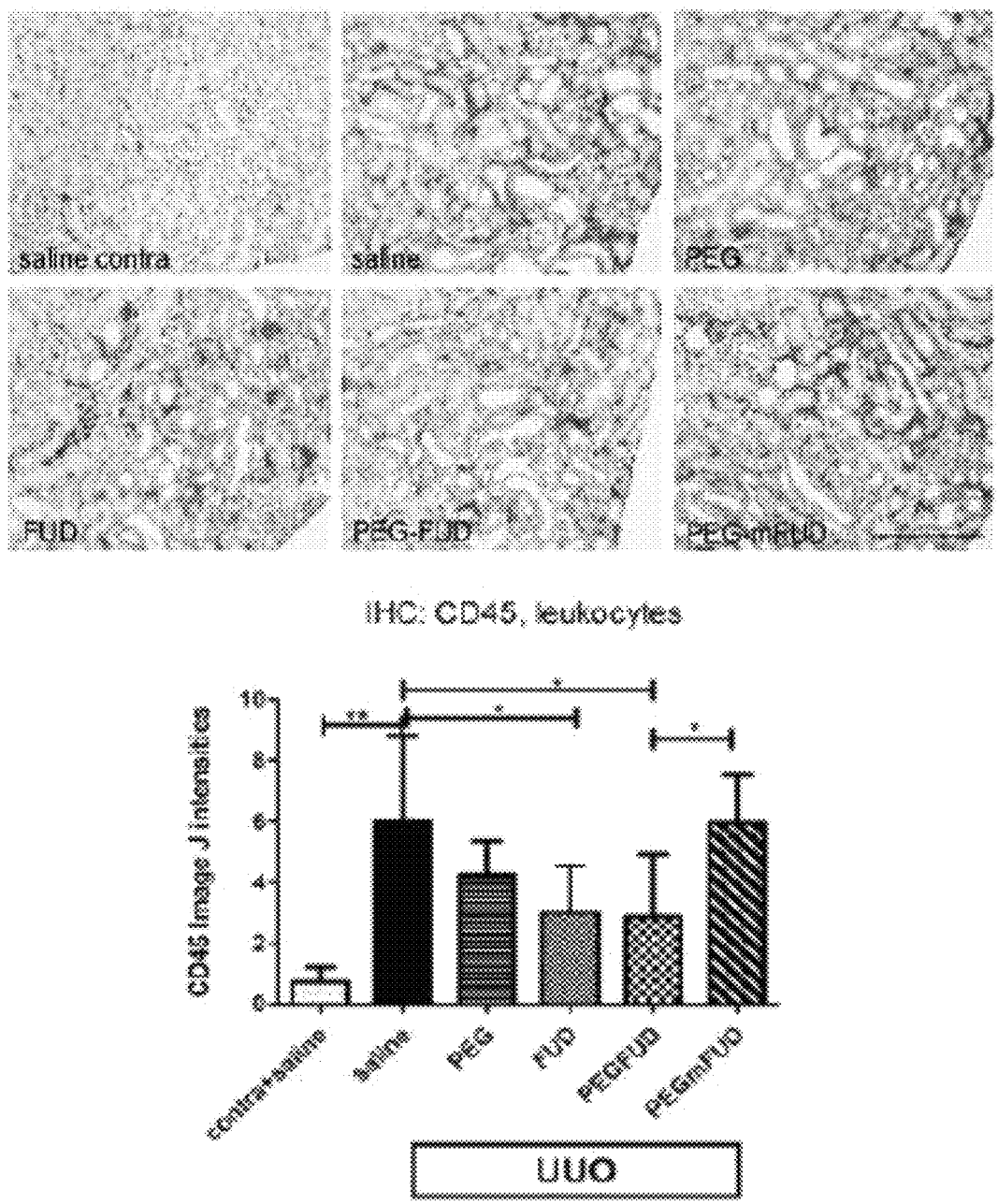
FIG. 29 shows representative images from the central cortex of 4 µm kidney sections stained with rat anti-mouse CD45 at 2.5 µg/ml. UUO and contralateral kidneys were stained simultaneously. Except for the contralateral kidney of saline treated mice, all other images are from UUO kidneys for comparison of treatment with saline, PEG, FUD, PEG-FUD and PEG-mFUD. Bar=200 µm. Quantitation of staining was performed using Image J and the mean of six images per treatment per cohort+/−SD is graphed. Significance is denoted as * $p<0.05$; ** $p<0.001$.

It was reported in other studies that a decrease in fibronectin was associated with decreased leukocyte infiltration. The representative images shown in FIG. 29 indicated a low level of leukocytes in the contralateral kidneys treated with saline, which was also representative of contralateral kidneys in all treatment groups. The corresponding UUO kidney section shows clear infiltration of leukocytes into the interstitium. Quantitation of staining by Image J, shows a 6-fold increase in CD45 staining in UUO compared to contralateral kidneys. There was a significant decrease in CD45 staining of approximately 50% with both FUD and PEG-FUD, and variability similar to that observed for collagen. There was no significant change with PEG or PEG-mFUD.

Example 9: Qualitative Histological Assessment

Figure 30:
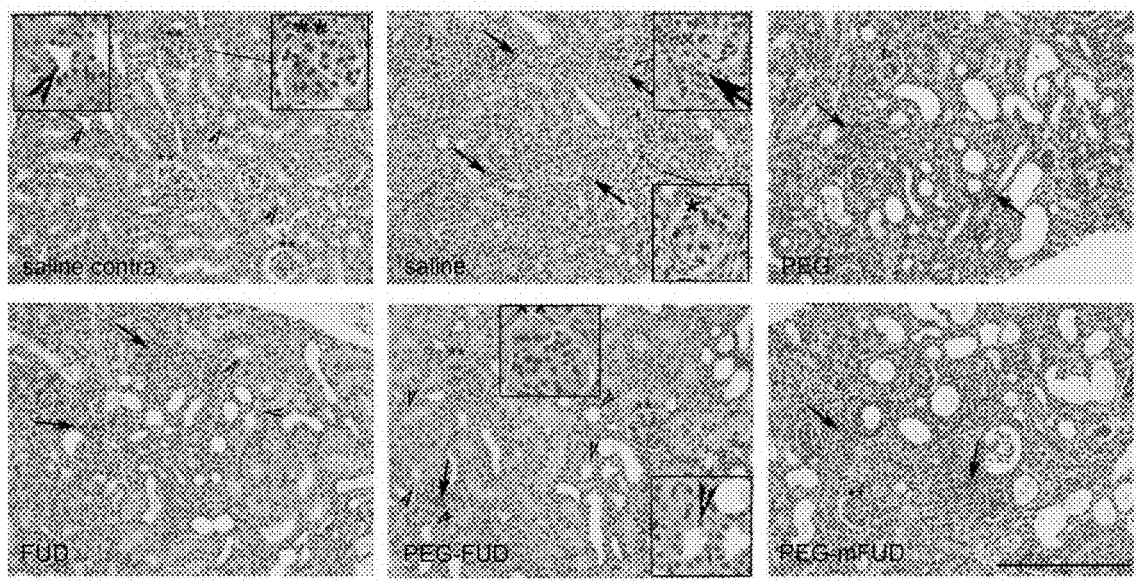
FIG. 30 shows representative images from the central cortex of 4 µm kidney sections stained with H&E. UUO and contralateral kidneys were stained simultaneously. Except for the contralateral kidney of saline treated mice, all other images are from UUO kidneys for comparison of treatment with saline, PEG, FUD, PEG-FUD and PEG-mFUD. Eosin staining was more prominent in the saline treated contralateral kidney, was associated with intact proximal tubules (arrowheads) and with defined glomeruli containing red blood cells (double asterisks). Hematoxilin staining associated with infiltrating cells, interstitial cell proliferation (arrows) and less defined glomeruli lacking red blood cells (single asterisk) were more prominent in the saline, PEG or PEG-mFUD-treated UUO kidneys. Diminished hematoxylin, increased eosin staining associated with tubular structures, and vascularized glomeruli similar to the contralateral kidney, were more apparent in the FUD and, to a greater extent, the PEG-FUD-treated kidneys, suggesting improvement in tubular and glomerular health. Bar=100 µm.

To investigate possible effects on viability of proximal tubules, sections sequential to those described above were stained for H&E. FIG. 30 shows representative images of H&E-stained sections from the central cortical regions of a contralateral kidney treated with saline (saline contra, left upper panel) in comparison with sections from UUO-treated kidneys (all other panels). Comparison of the contralateral and UUO kidneys from saline-treated mice indicates strong eosinophilic staining in the healthy kidney, which is lost with UUO treatment. Increased hematoxylin staining in the UUO kidneys is largely due to infiltration of leukocytes, loss of proximal tubules and proliferation of fibroblasts. Comparing treatments of UUO kidneys, we observed greater eosinophilic staining with FUD and PEG-FUD compared to saline; and similar to the contralateral kidney, clearer tubular preservation and vascularized glomeruli with PEG-FUD. Treatment with either PEG or PEG-mFUD did not increase eosinophilic staining and showed notably damaged tubules.

Discussion of Examples 4-9

We set out to ascertain whether the PEGylated form of FUD could reach injured kidneys and inhibit fibronectin deposition into the interstitium of UUO kidneys. In addition, we sought to determine if inhibition of fibronectin assembly would result in inhibition of kidney fibrosis, as ascertained by interstitial collagen deposition and leukocyte infiltration. Following subcutaneous administration, PEG-FUD was found intact in kidney extracts as per Western blotting analysis with some enrichment in UUO compared to contralateral kidneys. UUO kidneys presented the expected increase in fibronectin, collagen and CD45$^+$-leukocytes. Administration of PEG-FUD for 7 days, resulted in a significant decrease in fibronectin, collagen and leukocytes in UUO-treated kidneys. Qualitative evaluation of H&E-stained kidney sections suggested improvement in tubular atrophy with PEG-FUD treatment.

PEGylation often impedes or diminishes the interaction of the PEGylated molecule with its ligand. However, PEG-FUD retained activity and inhibited the incorporation of fibronectin into the ECM of fibroblasts and proximal tubular epithelial cells with IC50s similar to unconjugated FUD without affecting cell viability, as demonstrated previously for FUD. Thus, PEGylation did not affect FUD affinity for fibronectin and is expected to decrease both blood-derived and locally derived EDA+-fibronectin incorporation into tissues without deleterious effects on cell viability.

In vivo, PEG-FUD significantly decreased fibronectin in UUO kidneys, apparently to a greater extent than FUD itself. Because the intrinsic properties of the anti-FUD antibodies do not allow for detection of unconjugated FUD, we could only detect PEG-FUD and not FUD in kidney extracts. We attribute the preference of the anti-FUD antibodies for PEG-FUD to the fact that the antiserum was raised against FUD conjugated to KLH, which likely rendered the peptide into a conformation similar to that of PEGylated FUD. In any case, we cannot ascertain whether PEG-FUD is a more potent inhibitor of fibronectin deposition in vivo, or is retained better in diseased kidneys than FUD. Regardless, it is clear that PEG-FUD is a specific, potent inhibitor of fibronectin deposition into the interstitium of UUO kidneys.

The significant decrease in fibronectin precludes any concern that PEG-FUD would form complexes with fibronectin that would deposit in the interstitium and harm kidney tubules. If such complexes were present, there would have been increased staining for fibronectin, likely even higher than expected for UUO kidneys. Instead, we observed the opposite, decreased fibronectin with PEG-FUD treatment. In addition, using PEG-FUD to inhibit the deposition of fibronectin into the ECM did not cause any detectable levels of soluble fibronectin degradation, since intact fibronectin was detected in the kidney fractions, as well as in plasma. Indeed, the binding of PEG-FUD to fibronectin which, under in vitro conditions, is considerably tight (Kd approximately 10 nM), may actually protect at least the N-terminal 70 kDa fragment from degradation. That fibronectin is intact is of importance because fibronectin fragments are known to promote remodeling and pathological degeneration in some tissues.

Inhibiting fibronectin fibrillogenesis with PEG-FUD showed that fibronectin plays two important roles in the progression of kidney fibrosis. First, fibronectin serves a pivotal role in the deposition of collagens, as demonstrated in this study and the studies of others in vitro and in vivo. When we examined the effects of decreased fibronectin on the deposition of collagens I and III, as detected by picrosirius staining, we detected a significant decrease in collagens with treatment of FUD or PEG-FUD but not PEG or PEG-mFUD. Second, fibronectin has been associated with infiltrating leukocytes in a variety of conditions, serving as adhesive substratum and/or as ligand for Toll-like receptors. Similarly to collagen inhibition, FUD or PEG-FUD treatment was associated with a decrease in leukocyte infiltration in UUO kidneys suggesting that fibronectin plays a role in the inflammatory response in the kidney. Interestingly, the contralateral kidneys showed negligible levels of leukocyte infiltration with all treatments, suggesting no detectable immunoreactivity towards the peptides. Finally, H&E staining of UUO kidneys from mice treated with PEG-FUD, shows diminished tubular atrophy, possible improved glomerular vascularization, and confirms the reduction in leukocyte infiltration. However, because the contralateral kidney remains intact in the UUO model, renal function is not affected. Therefore, whether PEG-FUD improves renal function will be tested in a kidney disease model that affects both kidneys, such as the ischemia reperfusion injury, subtotal 5/6 nephrectomy, or chronic allograft nephropathy.

An important consideration is that fibronectin is intrinsic to wound healing mechanisms, forming part of the temporary matrix necessary for wound closure. Thus, a concern is that inhibiting fibronectin assembly may delay tubular regenerative capacity. These concerns may not be merited as mice with a conditional knock-out for plasma fibronectin, which constitutes about 50% of fibronectin deposited in tissues, show negligible hemostasis pathology. In addition, people with about half the normal levels of circulating fibronectin show no hemostasis abnormalities. Nevertheless, we were attentive to this issue and adjusted the timing of PEG-FUD delivery to target excess deposition of ECM while still allowing the healing process to occur and thus started administration three days post-UUO surgery. As noted, we detected the opposite in our pilot study, that is, protection from tubular atrophy with PEG-FUD and FUD.

Example 10: Fluorescence Imaging of PEG-FUD

Methods

Generation of Sulfo-Cy5 Labeled Drug: FUD and 10-40 kDa PEG-FUD conjugates were incubated with Sulfo-Cy5-NHS to label the drug with the fluorophore. A 2 mg/mL solution of drug dialyzed into 20 mM Tris (pH 8) was incubated with 1 eq of 10 mg/mL Sulfo-Cy5-NHS (Lumiprobe) stock solution dissolved in DMSO. The reaction was allowed to proceed at room temperature for 2 hrs. The reaction mixture was then dialyzed using 20 mM Tris (pH 8) and a 3000 MWCO dialysis membrane to remove unreacted label. The dialysis solution was replaced with fresh buffer after 6 hours and the dialysis was continued overnight (ON). The final reaction mixture was then purified using ion-exchange chromatography.

FPLC Purification and Separation of Sulfo-Cy5 labeled FUD and 10-40 kDa PEG-FUD: The FUD-Cy5 or PEG-FUD-Cy5 reaction mixture was loaded onto a HiTrap® Q HP anion exchange column (GE Healthcare Life Sciences, USA) initially equilibrated with Buffer A (20 mM Tris, pH 8.0). Upon sample injection, the column was washed with 2 CVs of Buffer A and the sample was eluted with a 10 CV gradient of Buffer B (1 M NaCl in 20 mM Tris, pH 8.0) at a flow rate of 0.5 mL/min. The fraction containing singly labeled drug was collected and snap frozen.

Preparation of Animal Experiment FUD and 10-40 kDa PEG-FUD Drug Dose: A 12.5 mg FUD equivalents per kg of mouse weight drug dose spiked with 1.5% Cy5 labeled drug was prepared by mixing an appropriate amount of unlabeled and labeled drug in a conical vial. The drug was then dialyzed ON into phosphate buffered saline (pH 7.4) using a 3000 MWCO dialysis membrane. The total volume of the dose was reduced to the appropriate value using a 3000 MWCO Amicon® Ultra-15 centrifugal unit. The final concentration of the drug was determined using a UV-vis spectrophotometer and the 646 nm extinction coefficient of Cy5, $\varepsilon = 271000$ $L \cdot mol^{-1} \cdot cm^{-1}$.

Fluorescence Imaging of Subcutaneous Dose Absorption: Female nude athymic mice were purchased from Envigo (Madison, Wis.) and housed in the Wisconsin Institutes for Medical Research animal facilities at the University of Wisconsin-Madison with ad-libitum access to food and water. Animals were maintained in humidity and temperature-controlled rooms under 12 h light/dark cycles. All work was conducted under protocol M005844, reviewed and approved by the University of Wisconsin-Madison Institutional Animal Care and Use Committee.

10 week old mice weighing 20-23 g were placed under 2% isoflurane anesthesia and positioned on their abdomen inside of an IVIS Spectrum In Vivo Imaging System. A 100 uL dose containing 0.27 mg (12.5 mg/kg) of FUD or FUD equivalents of 10-40 kDa PEG-FUD that was spiked with 1.5% Cy5 labeled drug was delivered subcutaneously between the shoulder blades of the animals (n=3 per treatment group). The animals were imaged before the injection, immediately following injection, and at time points of 30 minutes and 1, 3, 6, 12, 24, 36, and 48 hours. The animals were sacrificed following the last time point and their organs were harvested for ex vivo fluorescence imaging and drug extraction and quantification. LivingImage® (PerkinElmer) software was used to analyze the views of each animal group. The autodraw feature of the software set to a 5% threshold was used to create unique regions of interest (ROI) on each animal at t=30 mins views that were consistently applied to each subsequent time point views to quantify drug levels present at the site of injection. Baseline autoflorescence values calculated from ROIs applied to "before injection" views were subtracted from the values of each time point's animals. The ROI values obtained from the t=30 mins views were used to calculate % dose remaining for each subsequent time point.

Results

Figure 31:
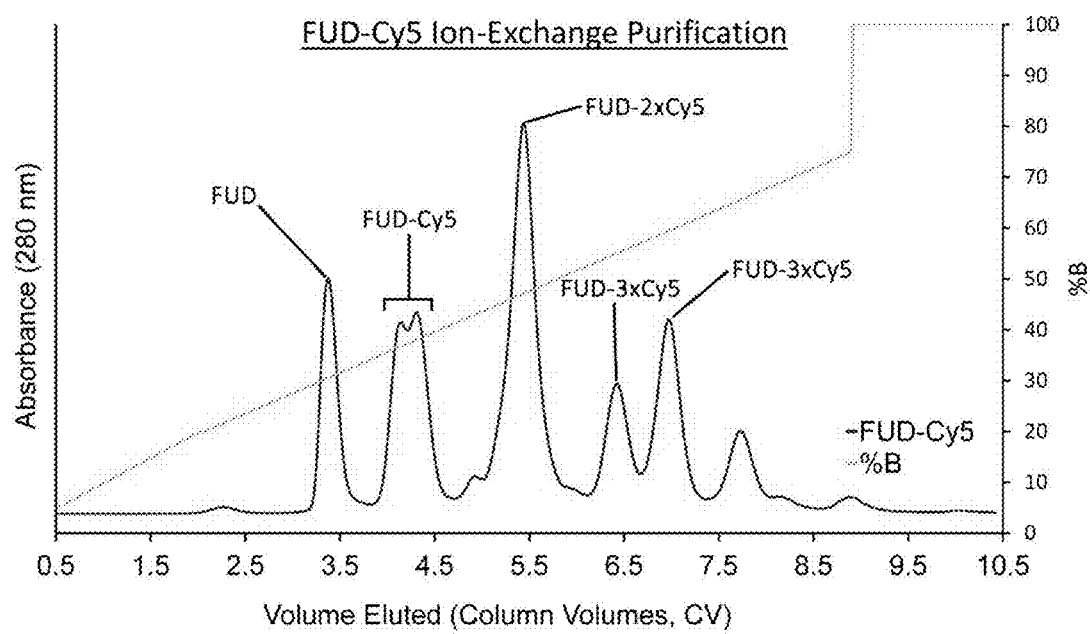
FIG. 31 shows FPLC ion exchange chromatogram showing isolation by fractionation of the singly labeled FUD-Cy5 conjugate.

FIG. 31 shows FPLC ion exchange chromatogram showing isolation by fractionation of the singly labeled FUD-Cy5 conjugate. An anionic exchanger combined with a mobile phase gradient of 20 mM Tris A side and 1 M NaCl B side were used to elute the labeled peptide and to separate it from other reaction product components via fractionation.

Figure 32:
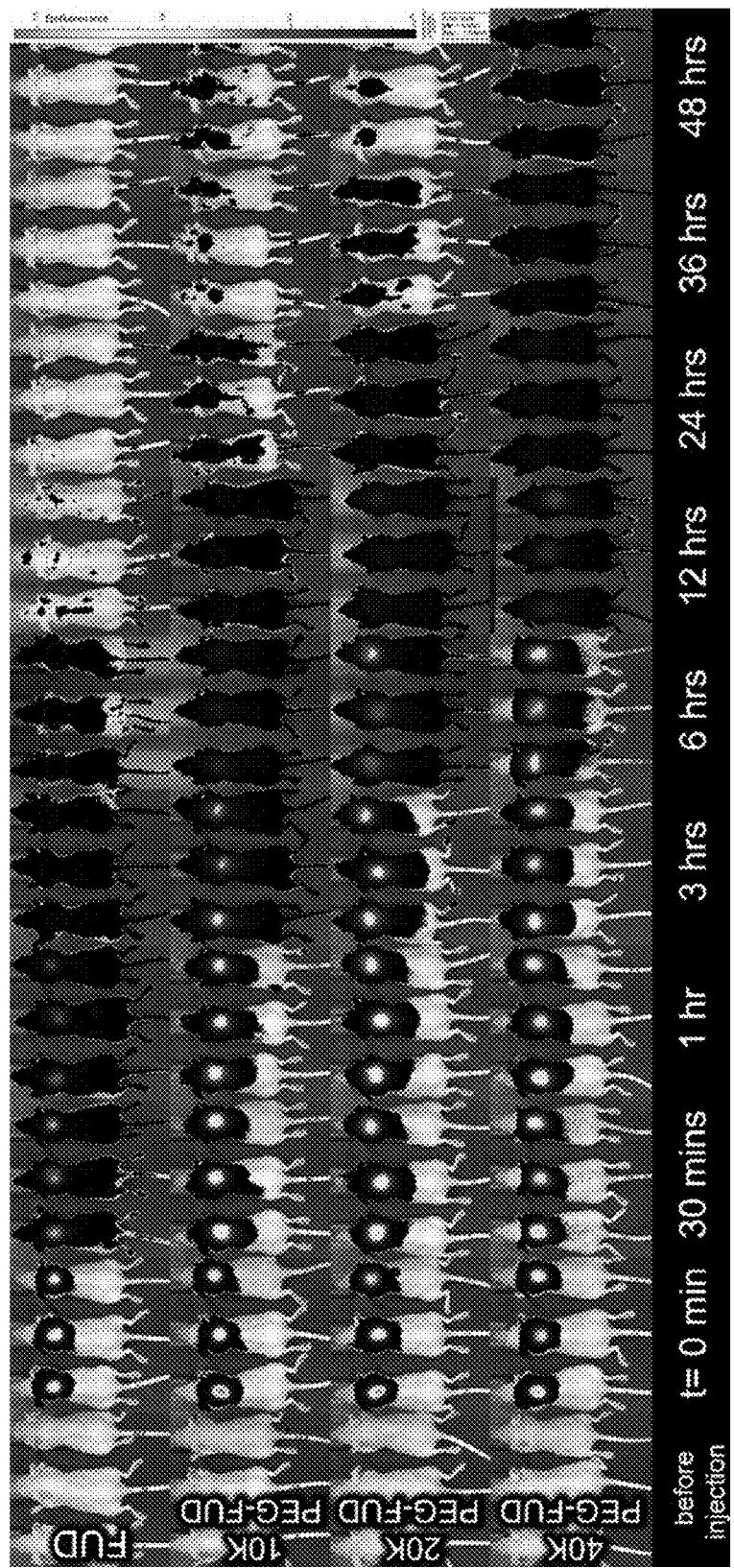
FIG. 32 shows IVIS fluorescence imaging of the absorption of subcutaneously delivered FUD or 10 kDa, 20 kDa, and 40 kDa PEG-FUD.

FIG. 32 shows IVIS Fluorescence imaging of the absorption of subcutaneously delivered FUD or 10 kDa, 20 kDa, and 40 kDa PEG-FUD. Each drug dose was spiked with 1.5% Sulfo-Cy5 labeled drug. The drug can be detected both at the site of injection and the general circulation at increasingly longer time points as the molecular weight of the PEG-FUD conjugate increases.

Figure 33:
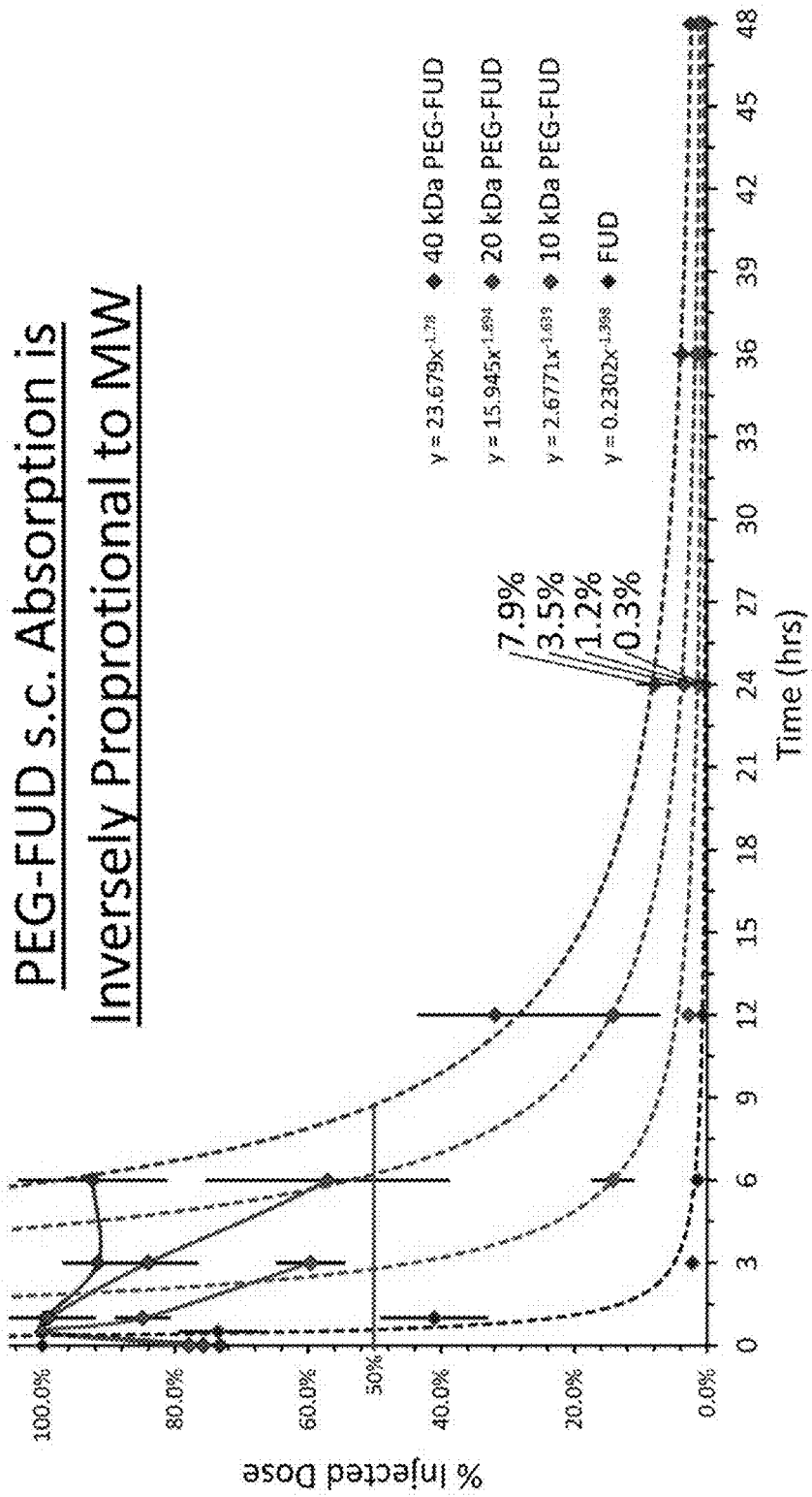
FIG. 33 shows quantification of FUD or 10 kDa, 20 kDa, and 40 kDa PEG-FUD drug levels present at the site of injection.

FIG. 33 shows quantification of FUD or 10 kDa, 20 kDa, and 40 kDa PEG-FUD drug levels present at the site of injection. Regions of interest were derived from t=30 minutes time point views and were applied uniquely to each animal in each time point's views. The rate of drug absorption is significantly reduced with increasingly larger molecular weight of each PEG-FUD conjugate. Apparent half-life of each drug was determined to be 35 mins, 2.8 hrs, 6.2 hrs, and 8.7 hrs and the % dose remaining at the site of injection after 24 hours was determined to be 0.3%, 1.2%, 3.5%, and 7.9% for FUD and 10 kDa, 20 kDa, and 40 kDa PEG-FUD, respectively.

Figure 34:
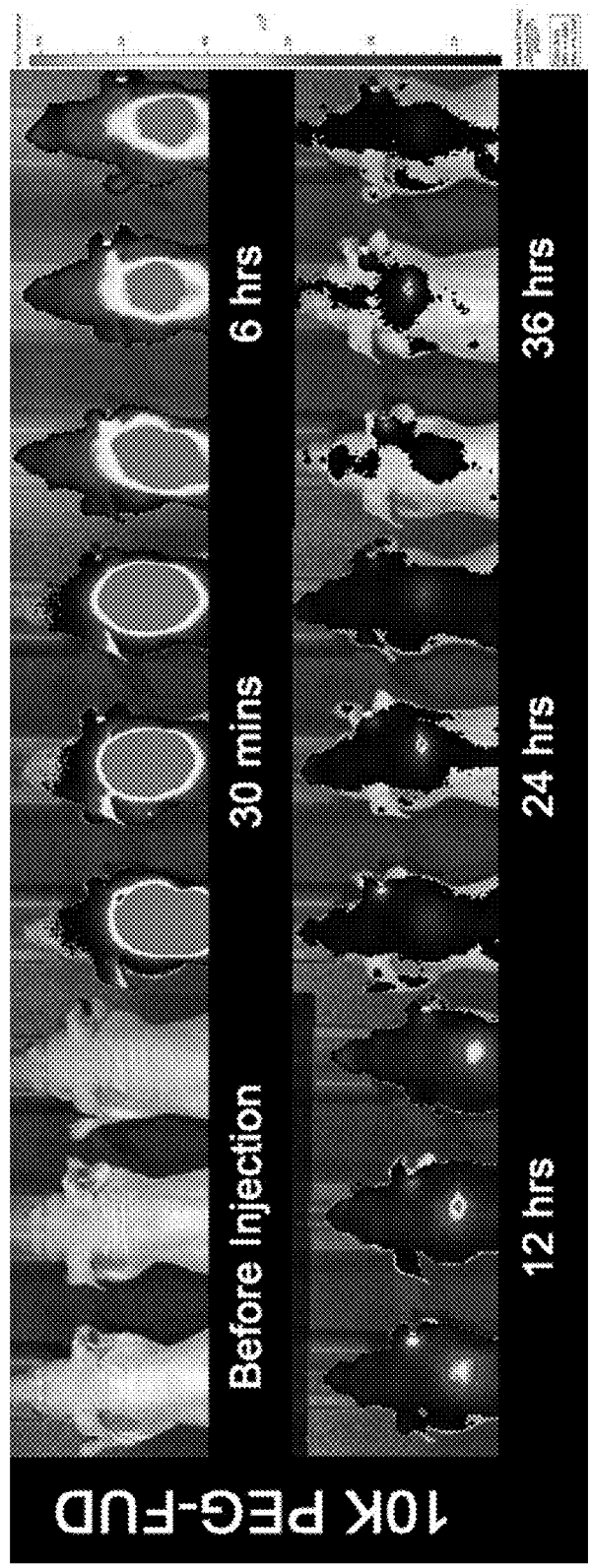
FIG. 34 shows migration of 10 K PEG-FUD into the site of injury.

FIG. 34 shows migration of 10 K PEG-FUD into the site of injury. Specifically, FIG. 34 shows the migration of PEG-FUD to fibronectin-rich wounds located on the right ear of the mice caused by tagging of the ear with a metal label. The mouse tagging was done several days before the administration of the drug. This figure shows evidence of a labeled PEG-FUD having potential as a diagnostic tool for trauma/fibrosis localization as well as that of other fibronectin-rich areas.

Example 11: PEG-FUD in a Murine Model of Bleomycin-Induced Pulmonary Fibrosis Methods Initiation of bleomycin-induced pulmonary fibrosis: Eight-week-old female C57BL/6 mice were purchased from Jackson Labs and housed in the Clinical Sciences Center animal facilities at the University of Wisconsin-Madison with ad-libitum access to food and water. Animals were maintained in humidity and temperature-controlled rooms under 12 h light/dark cycles. All work was conducted under protocol M005823, reviewed and approved by the University of Wisconsin-Madison Institutional Animal Care and Use Committee. All efforts were made to minimize suffering. The Bleomycin model is a rodent model representing a human equivalent of pulmonary fibrosis with the fibrotic response peaking between 14 and 21 days post-bleomycin installation. To initiate bleomycin injury, mice were anesthetized with ketamine (100 mg/kg) and xylazine (15 mg/kg) prior to delivering a single intratracheal dose of bleomycin (1 U/kg, Teva Pharmaceutical Industries, Ltd) reconstituted in 0.9% Normal Saline (NS) or NS alone as control.

Treatment strategy of subcutaneous PEG-FUD: On day three post-bleomycin treatment, mice were subject to a daily subcutaneous (SC) treatment with either PEG-FUD (12.5 mg/kg/day) or an equal dose of an inactive control peptide, PEG-mFUD, until day 13.

End-points for analysis: On day 14, mice were euthanized and lungs homogenized for hydroxyproline and western blot. Additionally, mouse survival by day 14 was compared between bleomycin PEG-FUD- and bleomycin PEG-mFUD-treated groups using Log-Rank test.

Separately, on day three post-bleomycin treatment, another animal set was treated with a single SC dose of PEG-FUD mixed with 25% Cy5-fluorophore labeled PEG-FUD or fully unlabeled PEG-FUD control (12.5 mg/kg). These mice were sacrificed seven days post-bleomycin treatment and their lungs, kidneys and livers imaged ex vivo using the fluorescence protocol on In Vivo Imaging System.

Hydroxyproline assay: Hydroxyproline assay was performed by Dounce homogenizing right lungs in deionized water, hydrolyzing in 6 N HCl for three hours at 120° C., drying for 45 min at 65° C., incubating in citrate-acetate buffer and chloramine-T for 20 min at room temperature, followed by Ehrlich's reagent for 15 min at 65° C. Subsequently, the samples were cooled to room temperature and the absorbance measured at 550 nm. Calculating the hydroxyproline content was done by using a standard curve generated from trans-4-Hydroxy-L-proline (Sigma Aldrich). Hydroxyproline results were analyzed using Students t-test with Bonferroni post-hoc test, comparing bleomycin- and PEG-FUD-treated mice to those treated with bleomycin and PEG-mFUD.

Western blot: Homogenized lung tissue was lysed for protein using 5% SDS/5 M Urea lysing buffer. The lysates were sonicated and boiled for 5 min prior to being subject to electrophoresis on polyacrylamide gels at 400 V for 2 hours and transferred at 100 V for 2.5 hours. Membranes were blotted with in-house made anti-FUD antibody produced in rabbit (0.7 µg/ml suspended in 2% bovine serum albumin) or β-actin housekeeping antibody produced in mouse (Sigma-Aldrich, 2 µg/ml suspended in 2% bovine serum albumin) and corresponding HRP-conjugated secondary antibody (1:3000). Blots were developed using an enhanced chemiluminescence (ECL) reaction (GE) and imaged on GE LAS4000 chemiluminescence imager to obtain images below the saturated threshold. ImageJ software was used for performing densitometry on the blots.

In Vivo Imaging System: Lungs, livers and kidneys of mice treated with bleomycin or NS and a single dose of SC Cy5-PEG-FUD or unlabeled PEG-FUD were imaged using the fluorescence protocol in the In Vivo Imaging System. Imaging was done with 640 nm excitation and 680 nm emission filters and 0.5 second exposure time.

Results

Figure 35:
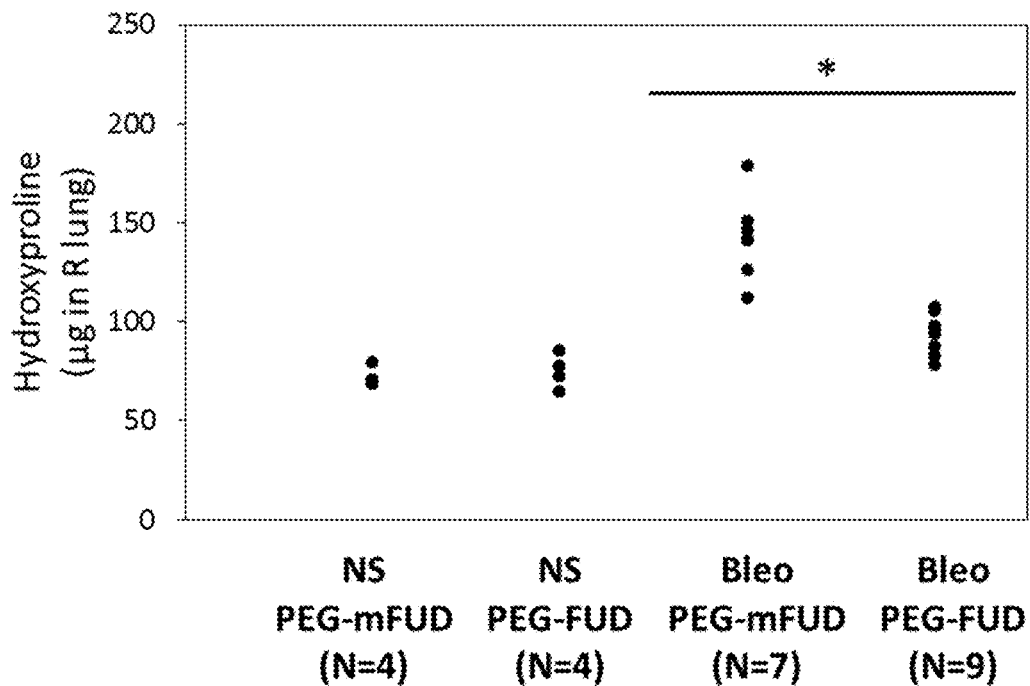
FIG. 35 shows quantification of collagen accumulation by hydroxyproline assay of right lung lysates obtained day 14 post-bleomycin and following day 3-13 daily PEG-FUD or PEG-mFUD control treatment. Student's t-test with Bonferroni correction ($p<0.025$) was applied.
Figure 36:
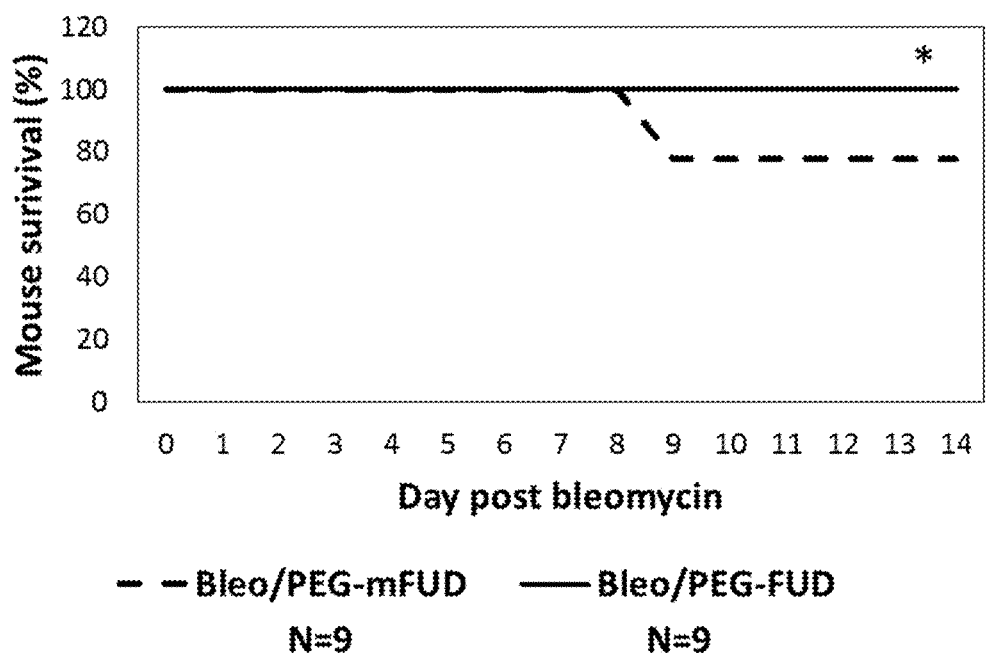
FIG. 36 shows mouse survival after 14 days post intratracheal administration of bleomycin and following day 3-13 daily PEG-FUD or PEG-mFUD control treatment. Log-rank test ($p<0.05$).

PEG-FUD treatment ameliorates the fibrotic response in bleomycin model of pulmonary fibrosis: First, the effect of Day3 to Day13 treatment with SC PEG-FUD bleomycin-induced pulmonary fibrosis was assessed. For this, the hydroxyproline assay (gold standard for measuring collagen content) was performed on the isolated right lungs of mice fourteen days post-bleomycin or NS treatment (treated with either PEG-FUD or PEG-mFUD). Hydroxyproline assay demonstrated a significant reduction of collagen accumulation in bleomycin-treated mice injected with PEG-FUD compared to bleomycin-treated mice injected with the control PEG-mFUD peptide (FIG. 35). The survival of bleomycin-treated mice subjected to PEG-FUD injections was compared PEG-mFUD injections. There was a marked increase in the survival of PEG-FUD-treated animals with 100% of this group surviving to the end of the 14-day trial compared with less than 80% (seven out of nine) of bleomycin and PEG-mFUD-treated controls (FIG. 36). Together, these results demonstrate that SC PEG-FUD administration from day 3 to day 13 after intratracheal bleomycin improves survival and the collagen accumulation that characterize pulmonary fibrosis.

Figures 37, 38:
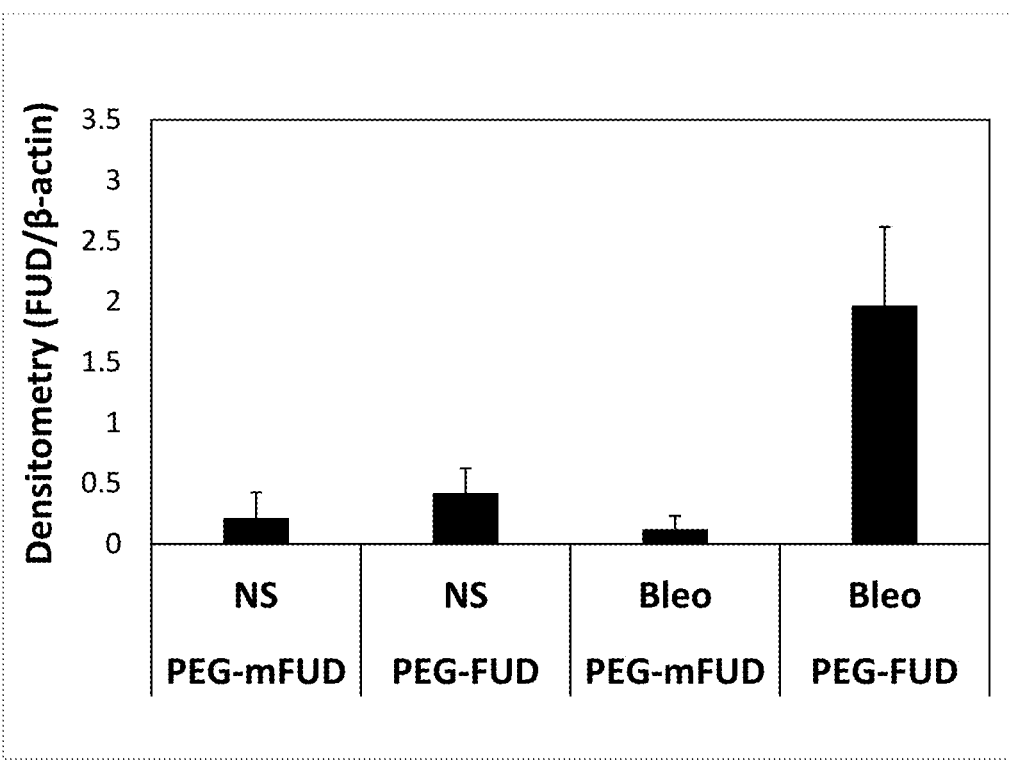
FIG. 37 shows three days after bleomycin treatment, mice were given daily subcutaneous injections of PEG-FUD or PEG-mFUD (control peptide) (12.5 mg/kg/day) until the 14-day end-point. Lung homogenates from these mice were subjected to polyacrylamide gel electrophoresis followed by Western blotting with rabbit-anti-FUD IgG at 0.7 µg/ml or mouse-anti-β-actin housekeeping antibody at 2 µg/ml followed by HRP-conjugated anti-rabbit IgG at 1:3000.
FIG. 38 shows quantification of Western blot densitometry performed using Image J from FIG. 37. Student's t-test with the Bonferroni correction ($p<0.025$) was applied.
Figure 39:
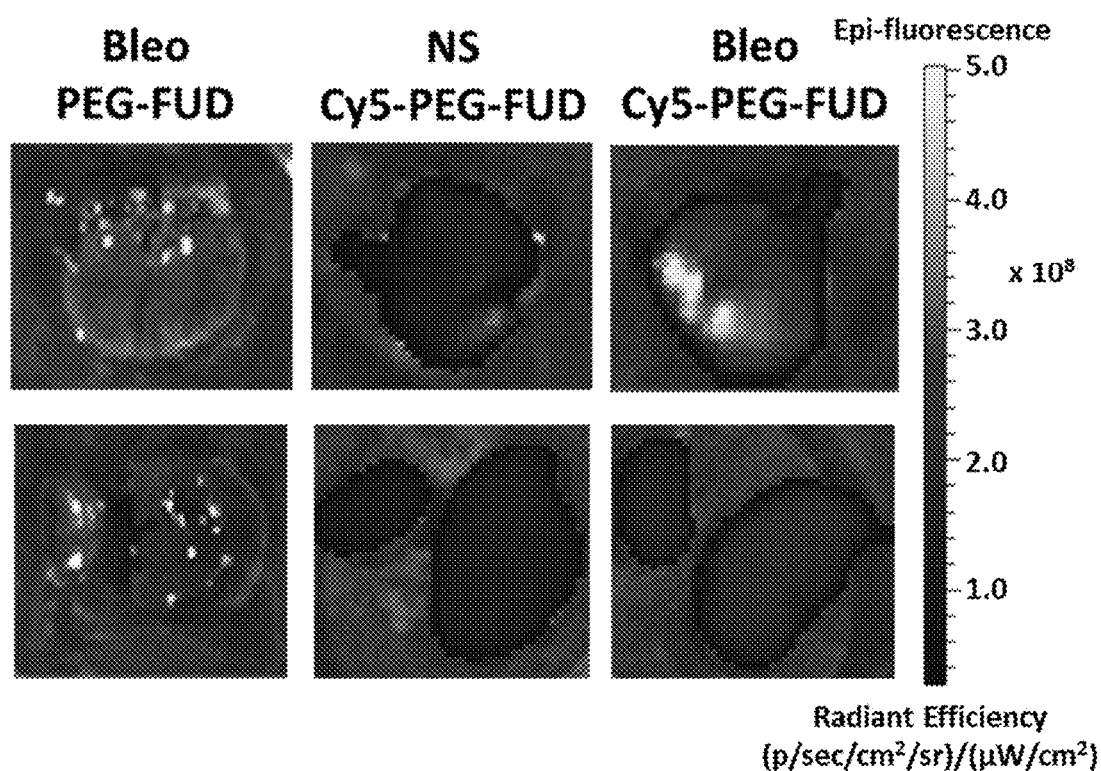
FIG. 39 shows three days after bleomycin treatment, mice were given a single subcutaneous injection of PEG-FUD or Cy5-PEG-FUD. Four days later, mouse organs were harvested and imaged using the fluorescence protocol on the In Vivo Imaging System.
Figure 40:
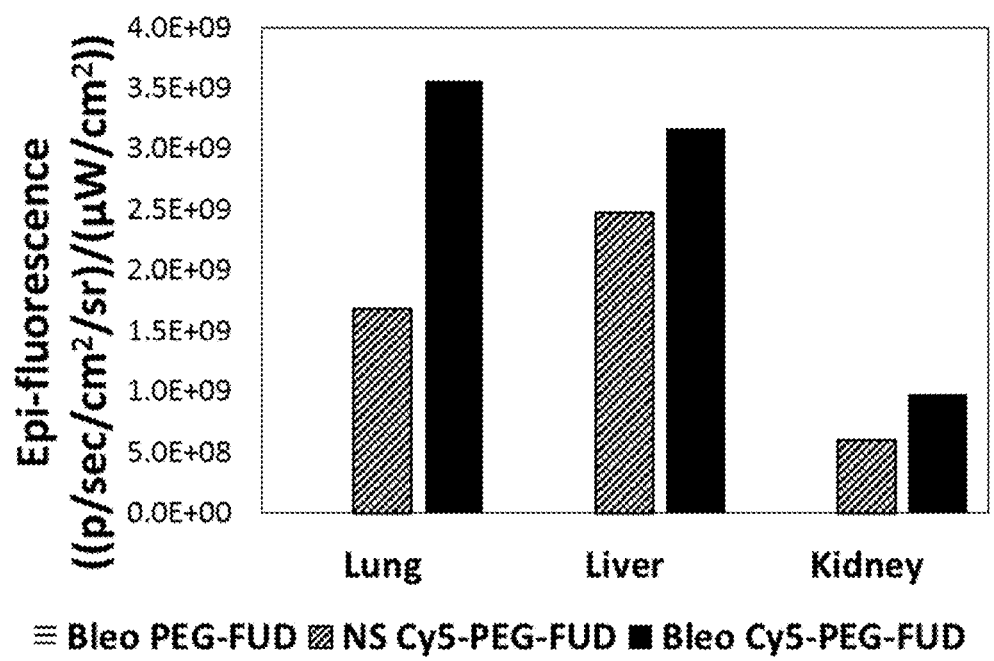
FIG. 40 shows Quantification of epi-fluorescence signal from FIG. 39.

PEG-FUD preferentially targets the injured lung following bleomycin-induced pulmonary fibrosis: In addition to determining the collagen content at the end of the 14-day bleomycin/PEG-FUD study, the amount of PEG-FUD peptide in the injured lungs was quantified by performing polyacrylamide gel electrophoresis on denatured and reduced right lung lysates followed by Western blotting using antibody against the FUD peptide. Western blots showed that PEG-FUD did have a modest amount of localization to uninjured lungs (0.9% NS intratracheal) after day 3-13 SC injection of PEG-FUD. In contrast, there was a striking increase in PEG-FUD accumulation in bleomycin-injured lungs isolated from Day 3-13 SC PEG-FUD-injected animals (FIG. 37 and FIG. 38). Given the stable injection doses between these two groups, this finding suggests that PEG-FUD selectively targets injured and repairing lung. To confirm this finding, PEG-FUD was N-terminally labeled with the fluorophore, Cy5, in order to allow for fluorescence-based organ-specific detection of the peptide (as described in [0125]). Three days following the intratracheal delivery of bleomycin or NS, mice were given a single SC injection of PEG-FUD spiked with 25% of Cy5-labeled PEG-FUD. Mice were sacrificed seven days post-bleomycin or NS treatment and their lungs, kidneys and livers imaged ex vivo using the In Vivo Imaging System. The imaging results revealed that epifluorescence more than doubled in the lungs of the mouse treated with bleomycin and Cy5-PEG-FUD compared to the NS-treated control. (FIG. 39, 40) Additionally, imaging of kidneys and livers of the same mice and demonstrated a slight increase of Cy5-PEG-FUD in the mouse intratracheally treated with bleomycin, possibly related to systemic effects from bleomycin administration. This data confirmed our initial findings that PEG-FUD preferentially targets injured and repairing tissues, including the bleomycin-treated lungs.

In summary, these studies show that SC PEG-FUD treatment initiated after the onset of bleomycin-induced lung injury and fibrosis, significantly improves survival and reduces overall lung fibrosis. Unexpectedly, there was a remarkable increase in the PEG-FUD accumulation in the injured tissues post bleomycin treatment. These exciting results suggest that not only should PEG-FUD be used as a treatment against human forms of pulmonary fibrosis, including IPF, but also may have utility as a probe for areas of injured and repairing tissue, such as that seen in active pulmonary (or other organ) fibrosis, as well as potential to identify clot formation and wound healing.

The use of the terms "a" and "an" and "the" and similar referents (especially in the context of the following claims) are to be construed to cover both the singular and the plural, unless otherwise indicated herein or clearly contradicted by context. The terms first, second etc. as used herein are not meant to denote any particular ordering, but simply for convenience to denote a plurality of, for example, layers. The terms "comprising", "having", "including", and "containing" are to be construed as open-ended terms (i.e., meaning "including, but not limited to") unless otherwise noted. Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. Any combination of the above-described elements in all possible variations thereof is encompassed by the invention unless otherwise indicated herein or otherwise clearly contradicted by context.

The invention claimed is:

1. A mono-end-PEGylated functional upstream domain (FUD), wherein the FUD peptide comprises SEQ ID NO: 1, and wherein the PEG is covalently linked to the N-terminus of FUD.

2. The mono-end-PEGylated FUD of claim 1, wherein the PEG has a molecular weight of 10-40 kDa.

3. The mono-end-PEGylated FUD of claim 1, further comprising a detectable label.

4. A pharmaceutical composition comprising the mono-end-PEGylated FUD of claim 1 and a pharmaceutically acceptable excipient.

5. The pharmaceutical composition of claim 4 in the form of a parenteral pharmaceutical composition.

6. The pharmaceutical composition of claim 4, further comprising a second therapeutic agent that is an anti-fibrotic agent, an anti-cancer agent, or a combination thereof.

7. A method of inhibiting fibrosis in a subject in need thereof, comprising
administering to the subject a therapeutically effective amount of the mono-end-PEGylated FUD of claim 1.

8. The method of claim 7, wherein administration is subcutaneous administration.

9. The method of claim 7, wherein the fibrosis comprises organ fibrosis.

10. The method of claim 9, wherein the organ is liver, kidneys, and lungs.

11. The method of claim 10, wherein the patient is suffering from chronic kidney disease.

12. The method of claim 11, wherein the chronic kidney disease is associated with kidney transplant.

13. The method of claim 9, wherein the patient is suffering from organ fibrosis associated with glomerulosclerosis, pulmonary fibrosis, peritoneum fibrosis, myocardial fibrosis, dermatofibrosis, post-surgery adhesions, benign prostatic hypertrophy, skeletal muscle fibrosis, dermatosclerosis, multiple sclerosis, pancreatic fibrosis, liver cirrhosis, myosarcoma, neurofibroma, diabetic nephropathy, Alzheimer's disease, or vascular fibrosis.

14. The method of claim 7, wherein the patient is a human patient suffering from idiopathic pulmonary fibrosis.

15. The method of claim 7, further comprising administering a second therapeutic anti-fibrotic agent for the treatment of organ fibrosis.

16. A method of inhibiting fibrosis associated with cancer metastasis, comprising administering to a subject in need thereof the mono-end-PEGylated FUD of claim 1.

17. The method of claim 16, wherein the cancer is ovarian, pancreatic or breast cancer.

18. The method of claim 16, further comprising administering an anti-cancer agent.

19. A method of binding fibronectin associated with injured tissue or tissue to be repaired in an individual in need thereof, comprising administering to the individual a diagnostic amount of the mono-end-PEGylated FUD of claim 1 wherein the mono-end-pegylated FUD binds fibronectin.

20. The method of claim 19, wherein the mono-end-PEGylated FUD comprises a detectable label.

\* \* \* \* \*

SEQUENCE LISTING

```
<160> NUMBER OF SEQ ID NOS: 2

<210> SEQ ID NO 1
<211> LENGTH: 49
<212> TYPE: PRT
<213> ORGANISM: human

<400> SEQUENCE: 1

Lys Asp Gln Ser Pro Leu Ala Gly Glu Ser Gly Glu Thr Glu Tyr Ile
1               5                   10                  15

Thr Glu Val Tyr Gly Asn Gln Gln Asn Pro Val Asp Ile Asp Lys Lys
                20                  25                  30

Leu Pro Asn Glu Thr Gly Phe Ser Gly Asn Met Val Glu Thr Glu Asp
            35                  40                  45

Thr

<210> SEQ ID NO 2
<211> LENGTH: 22
<212> TYPE: PRT
<213> ORGANISM: human
```

```
<400> SEQUENCE: 2

Asp Lys Lys Leu Pro Asn Glu Thr Gly Phe Ser Gly Asn Met Val Glu
1               5                   10                  15

Thr Glu Asp Thr Lys Ala
                20
```